United States Patent
Blasetto et al.

(10) Patent No.: US 11,031,104 B2
(45) Date of Patent: *Jun. 8, 2021

(54) SYSTEMS AND METHODS FOR DISPENSING A STATIN MEDICATION OVER THE COUNTER

(71) Applicant: AstraZeneca UK Ltd., London England (GB)

(72) Inventors: James Blasetto, Chadds Ford, PA (US); Judy Firor, Landenberg, PA (US); David Guiga, West Chester, PA (US); William Mongan, Malvern, PA (US); Robert Prybolsky, West Chester, PA (US); Richard L. Skelly, Flourtown, PA (US)

(73) Assignee: ASTRAZENECA UK LTD., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/791,745

(22) Filed: Feb. 14, 2020

(65) Prior Publication Data
US 2020/0294631 A1 Sep. 17, 2020

Related U.S. Application Data

(63) Continuation of application No. 15/385,747, filed on Dec. 20, 2016, now Pat. No. 10,600,502.

(51) Int. Cl.
*G16H 10/20* (2018.01)
*G06F 19/00* (2018.01)
(Continued)

(52) U.S. Cl.
CPC ......... *G16H 10/20* (2018.01); *G06F 19/3456* (2013.01); *G16H 10/60* (2018.01);
(Continued)

(58) Field of Classification Search
None
See application file for complete search history.

(56) References Cited

U.S. PATENT DOCUMENTS

| 7,493,264 B1 | 2/2009 | Kelly et al. |
| 2005/0108053 A1 | 5/2005 | Jones |

(Continued)

FOREIGN PATENT DOCUMENTS

| WO | WO 2010/041052 A1 | 4/2010 |

OTHER PUBLICATIONS

International Search Report and Written Opinion for International Patent Application No. PCT/EP2017/083774 dated May 7, 2018, 17 pages.
(Continued)

*Primary Examiner* — Devin C Hein
(74) *Attorney, Agent, or Firm* — Morgan, Lewis & Bockius LLP; Brett A. Lovejoy; Andrew J. Antczak

(57) ABSTRACT

Systems and methods are provided for over the counter statin delivery to a subject. Survey results from the subject are run against a first plurality of filters. When a filter in the first plurality of filters is fired, the subject is deemed not qualified. The survey results are also run against a second plurality of filters. When a respective filter in the second plurality is fired, the subject is provided with a corresponding warning. The method proceeds to a fulfillment process when no filter in the first plurality fires and the subject has acknowledged each warning associated with each fired filter in the second plurality. The fulfillment stores the composition order, communicates a drug facts label for the statin to the subject, and authorizes, upon subject confirmation that the label has been read, provision of the statin to the subject, the authorization including a destination associated with the subject.

33 Claims, 33 Drawing Sheets

(51) Int. Cl.
*G16H 10/60* (2018.01)
*G16H 20/10* (2018.01)
*G16H 70/20* (2018.01)
*G16H 20/13* (2018.01)
*G06Q 50/22* (2018.01)

(52) U.S. Cl.
CPC ............ *G16H 20/10* (2018.01); *G16H 20/13* (2018.01); *G16H 70/20* (2018.01); *G06Q 50/22* (2013.01)

(56) References Cited

U.S. PATENT DOCUMENTS

2011/0166876 A1   7/2011   Chapman
2011/0178812 A1   7/2011   Lindsay

OTHER PUBLICATIONS

Ramkumar, S. et al., Acta Cardiol. Sin., 32(6):631-39 (2016).
Barlas S. FDA Considers a New Paradigm for Over-the-Counter Medications: More Power-but More Burdens-for Pharmacists and Pharmacies. P T. May 2012;37(5):300-5. PubMed PMID: 22876088; PubMed Central PMCID: PMC3411219.
Crestor, Full Prescribing Information, 2012, AstraZeneca Pharmaceuticals LP.
Dyer O., BMJ, 330(7484):164 (2005).
May 9, 2013, power point presentations from the Engelberg Center for Health Care Reform.
Pfizer Wants Atorvastatin Available Over the Counter—Medscape—Aug. 4, 2011, downloaded from the Internet Nov. 30, 2018.
PR Newswire Association, "Americans Should Pay More Attention to Over-the-Counter (OTC) medicine Labels According to New Survey", Oct. 15, 2015 (citing McNeil Consumer Healthcare research).

(B)

↓
418

Run all or a portion of the first plurality of survey results against a second plurality of filters 220 of a second category class. When a respective filter 222 in the second plurality of filters is fired, the subject is provided with a warning 226 corresponding to the respective filter. — 420

> The second plurality of filters comprises a total cholesterol level filter, an age filter, a drug interaction filter, an alcohol consumption filter, an adverse reaction filter, an atherosclerotic cardiovascular event filter, and a pooled cohort equation filter. — 422

>> The pooled cohort equation filter incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value, the pooled cohort equation filter is deemed fired. — 424

>>> The risk for the atherosclerotic cardiovascular disease is a lifetime risk, five year risk, or 10 year risk. — 426

>>> The pooled cohort equation is implemented as a multivariable Cox proportional hazard regression. — 428

>>> The risk for the atherosclerotic cardiovascular disease is a 10 year risk, and the first threshold value is 7.5 percent. — 430

>> The risk for the atherosclerotic cardiovascular disease is a 10 year risk and the first threshold value of the pooled cohort equation filter is 7.5 percent, the total cholesterol level filter is fired when the first plurality of survey results indicates that the subject has a total cholesterol of less than 130 mg/dl or greater than 275 mg/dl, the age filter is fired when the first plurality of survey results indicates that the subject is a woman that is aged 49 or less or aged 76 or more, and the age filter is fired when the first plurality of survey results indicates that the subject is a man that is aged 39 or less or aged 66 or more. — 432

> The drug interaction filter is fired when the first plurality of survey results indicates that the subject is presently taking a blood thinner, warfarin, an HIV/AIDS medication, colchicine, a Hepatitis medication, a cholesterol lowering medication, itraconazole, ketoconazole, or fluconazole, and the alcohol consumption filter is fired when the first plurality of survey results indicates that the subject consumes an average of three or more servings of alcohol per day.

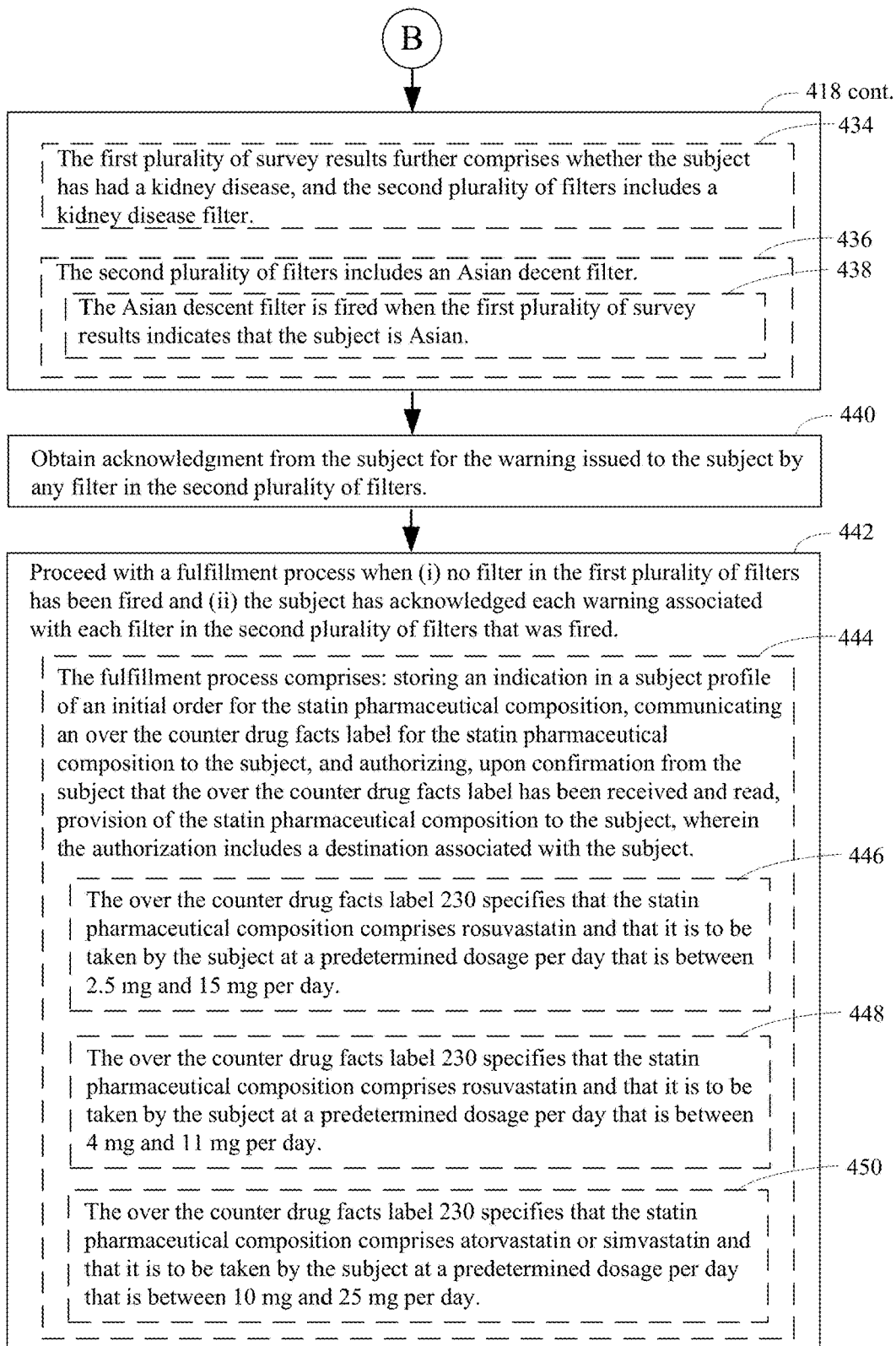

(D)

460

Responsive to receiving a re-order request from the subject for the statin pharmaceutical composition, a procedure is performed. The procedure comprises (i) conducting a second survey of the subject thereby obtaining a second plurality of survey results, wherein the second plurality of survey results comprises: whether the subject has experienced a muscle irregularity since taking the statin pharmaceutical composition, whether the subject is pregnant, whether the subject is taking a medication that interacts with the statin pharmaceutical composition, and whether the subject had an atherosclerotic cardiovascular event or a heart procedure since last ordering the statin pharmaceutical composition. The procedure further comprises running all or a portion of the second plurality of survey results against a third plurality of filters, wherein, when a respective filter in the third plurality of filters is fired, the subject is provided with a warning corresponding to the respective filter. The third plurality of filters comprises: the pregnancy filter, a muscle irregularity filter, a second drug interaction filter, and an atherosclerotic cardiovascular event filter. The procedure further comprises obtaining, when the re-fulfillment process is not terminated, acknowledgment from the subject for each warning issued to the subject by any filter in the third plurality of filters. The procedure further comprises proceeding with the re-fulfillment process when (i) the re-fulfillment process is not already terminated by the firing of a filter in the third plurality of filters and (ii) the subject has acknowledged each warning associated with each filter in the third plurality of filters that was fired and that is associated with a warning. The re-fulfillment process further comprises storing an indication in a subject profile of a re-order for the statin pharmaceutical composition, communicating an over the counter drug facts label for the statin pharmaceutical composition to the subject, and authorizing, upon confirmation from the subject that the over the counter drug facts label has been received and read, a re-order provision of the statin pharmaceutical composition to the subject, wherein the authorization includes a destination of the subject.

462

The muscle irregularity filter is fired when the second plurality of survey results indicates that the subject has experienced an unexplained muscle cramp or weakness since taking the statin pharmaceutical composition, the pregnancy filter is fired when the second plurality of survey results indicate that the subject is pregnant and results in termination of the re-fulfillment procedure, and the second drug interaction filter is fired when the second plurality of survey results indicates that the subject is presently taking cyclosporine, a blood thinner, warfarin, an HIV/AIDS medication, or a cholesterol lowering medication.

Fig. 4E

To see if Crestor OTC is right for you, there are 3 numbers you will need to have before you can proceed:

1. Your blood pressure (from your own measurement or from your doctor in the past 12 months)
2. Your total cholesterol (from a blood test)
3. Your HDL level (your "good cholesterol" number from a blood test)

Are you pregnant, think you may be pregnant, breastfeeding, or do you plan to become pregnant? — 208
more info You can't use Crestor OTC if you have any severe and serious disorder of the liver, like cirrhosis or hepatitis.

Why is this important?

- Very rarely serious liver injury has happened with prescription cholesterol lowering drugs You can't use Crestor OTC if you are taking cyclosporine, a drug used primarily in people who have had organ transplants Why is this important?

- Cyclosporine may significantly increase the blood levels of active ingredient in CRESTOR OTC

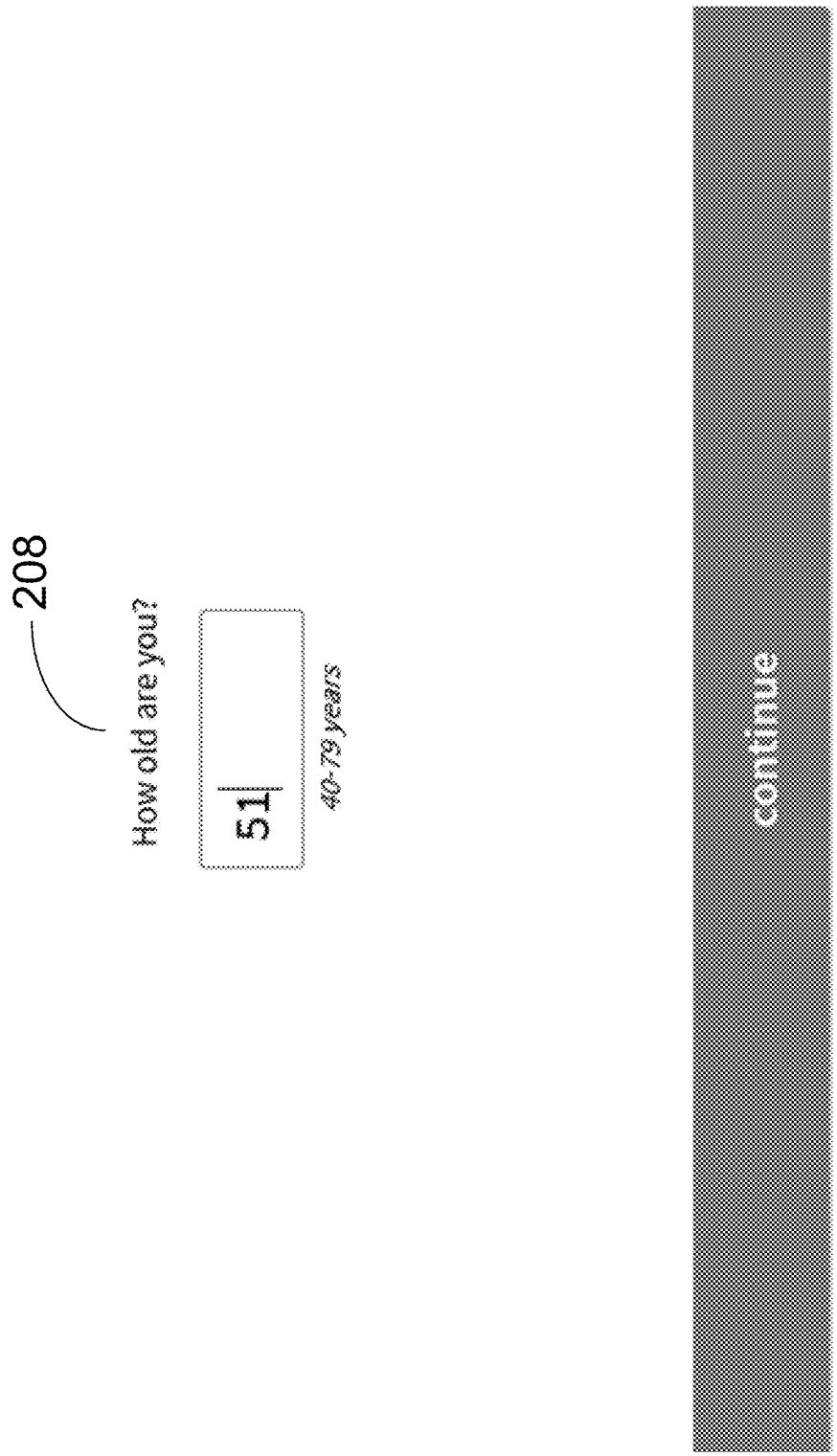

What is your total cholesterol level? — 208 more info

What is your systolic blood pressure (the first and larger of the two numbers)? — 208 more info

*Please enter a number*
*90-200 mmHg*

Fig. 5L

MORE INFORMATION

High blood pressure is also referred to as "hypertension" by many people in the medical world. A dietary or herbal supplement is not considered a "medication" for high blood pressure here when selecting your response.

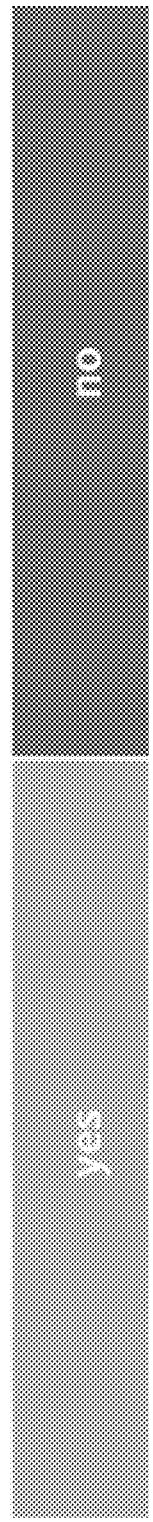

Do you drink 3 or more glasses of alcohol every day?
more info
— 208

208

Are you taking any of the following medications?

* Warfarin (a blood thinner),
* Colchicine (a gout medicine),
* Hepatitis or HIV/AIDS medication,
* Another medication to lower cholesterol,
* Certain anti-fungal medicines (such as itraconazole, ketoconazole, and fluconazole)

more info yes | no

Taking CRESTOR OTC with certain other medicines may affect each other causing side effects. CRESTOR OTC may affect the way other medicines work, and other medicines may affect how CRESTOR OTC works. A dietary or herbal supplement is not considered a "medication" here when selecting your response.

Lower Risk SEE YOUR DOCTOR

CRESTOR OTC may not be right for you. Based on your answers, you have a lower cardiovascular risk in the next 10 years. You can recheck periodically if CRESTOR OTC is right for you, as your risk is likely to change as you get older or your medical status changes.

If you still wish to get CRESTOR OTC now, you need to see your healthcare professional first. ONLY then can you get CRESTOR OTC.

Have you and your doctor already discussed Crestor OTC, and has your doctor said it is OK for you to take Crestor OTC?

Doctor's Name:

Doctor's name

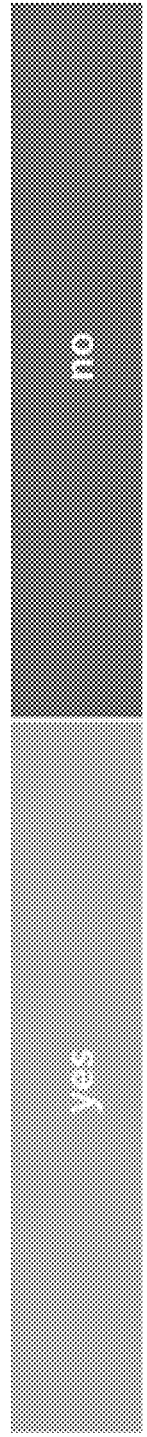

yes | no

Fig. 6

Crestor OTC Assessment Results (12/9/2016)

Dear Doctor,
I'm interested in CRESTOR OTC 5mg tablets, but based on my responses to the questions below, I was told I need to get my medical professional's consent before I can purchase CRESTOR OTC.

| Questions | Response | |
|---|---|---|
| Are you male or female? | Male | |
| How old are you? | 51 | |
| Which best describes your race? | White | |
| What is your total cholesterol level? | 160 | 2.5% |
| What is your HDL (high-density lipoprotein) level? | 50 | 10-year cardiovascular risk estimate* |
| What is your systolic blood pressure (the first and larger of the two numbers)? | 120 | |
| Are you currently taking any medications for high blood pressure? | No | |
| Do you have diabetes? | No | |
| Do you smoke? | No | |

*Estimated based on ACC/AHA ASCVD Risk Estimator

| Additional questions triggering doctor discussion | Response | No / Yes |
|---|---|---|
| Have you ever had a heart attack, stroke, or an operation or procedure on your heart? | No | ● |
| Are you pregnant, think you may be pregnant, breastfeeding, or do you plan to become pregnant? | No | ● |
| Do you have liver disease? | No | ● |
| Are you taking cyclosporine (a medication for your immune system)? | No | ● |
| Do you have kidney disease? | No | ● |
| Do you drink 3 or more glasses of alcohol every day? | No | ● |
| Have you had a bad/serious reaction to any other cholesterol lowering medication you took before? | No | ● |
| Are you taking any of the following medications? Warfarin (a blood thinner), Colchicine (a gout medicine), Hepatitis or HIV/AIDS medication, Another medication to lower cholesterol, Certain anti-fungal medicines (such as itraconazole, ketoconazole, and fluconazole) | No | ● |

Fig. 7

| | Crestor (rosuvastatin) | Lipitor (atorvastatin) | Zocor (simvastatin) | Pravachol (pravastatin) | Lescol XL (fluvastatin) | Livalo (pitavastatin) | Mevacor (lovastatin) |
|---|---|---|---|---|---|---|---|
| active liver disease | x | x | x | x | x | x | x |
| pregnant or may become pregnant | x | x | x | x | x | x | x |
| nursing mothers | x | x | x | x | x | x | x |
| hypersensitivity | x | x | x | x | x | x | x |
| cyclosporine | | | x | | | x | |
| gemfibrozil, danazol | | | x | | | | |
| strong CYP3A4 inhibitors | | | x | | | | x |

Fig. 8

SYSTEMS AND METHODS FOR DISPENSING A STATIN MEDICATION OVER THE COUNTER

CROSS REFERENCE TO RELATED APPLICATION

This application is continuation of U.S. patent application Ser. No. 15/385,747, entitled "SYSTEMS AND METHODS FOR DISPENSING A STATIN MEDICATION OVER THE COUNTER," filed Dec. 20, 2016, which is hereby incorporated by reference in its entirety.

TECHNICAL FIELD

The present disclosure relates generally to systems and methods for qualifying a human subject for delivery of a statin pharmaceutical composition without a prescription to treat or prevent atherosclerotic cardiovascular disease, e.g., by lowering cholesterol.

BACKGROUND

Cardiovascular disease remains the leading global cause of death, claiming more lives than all forms of cancer combined. The number of cardiovascular deaths is expected to increase to approximately 24 million annually by 2030. The direct and indirect annual costs total more than $316 billion dollars. This exceeds the entire GDP of all the world's countries except the top 30 countries.

Statins have been a cornerstone therapy for fighting heart disease for nearly three decades. The totality of evidence for reducing cardiovascular disease events is second to none in all of medicine. Statins are still the most prescribed class of medicine.

Despite the fact that many statins will be generically available off patent in the United States and other markets by 2017, it is expected that prevalence of cardiovascular disease will continue. That is, that heart disease will remain. The next-generation is showing clear signs they are going to develop cardiovascular disease at high prevalence levels and need help. Although novel therapies are materializing to address cardiovascular disease, it is expected that such novel therapies will be combined with statins, not replace them. Thus, it is expected that statins will remain a cornerstone therapy for cardiovascular disease for the foreseeable future.

Unfortunately, long-term trends demonstrate many people avoid prescription medications, including statins. One approach to making statins more available is to make then available without a prescription, e.g., over the counter ("OTC"). However, because statins cause serious adverse effects in certain patients, the population receiving the drug should be carefully selected and monitored. Ramkumar S. et al., Acta Cardiol. Sin., 32(6):631-39 (2016). This is why statin distribution has traditionally been regulated through exclusive prescription access. In order to ensure the safety of OTC distribution of statins, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey", Oct. 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Prior attempts to improve self-selection and safe use of statins OTC have met with failure. For example, Pfizer announced in 2011 its intention to switch Lipitor from prescription-only to OTC status. Sett OTC bulletin, 16 Nov. 2011, page 7. Pfizer abandoned its attempt to switch Lipitor from prescription-to-OTC (over the counter) status in the United States in 2014. Specifically, a phase 3 "actual use" trial intended to simulate the OTC use of Lipitor (atorvastatin calcium) 10 mg, completed in December 2014, failed to meet its primary objectives on the basis that patient compliance with the direction to check their low-density lipoprotein cholesterol (LDL-C) level and, after checking their LDL-C level, take appropriate action based on their test results was unsatisfactory. In fact, to date, a statin has never been granted OTC status in the United States, and it is over 15 years since Bristol-Myers Squibb and Merck & Co failed in their attempts to switch Pravachol to OTC.

More than a third of American adults are eligible to take cholesterol-lowering medications under the current guidelines or already taking them. Yet, nearly half of this group is not, according to a report by CDC researchers in the Morbidity and Mortality Weekly Report (MMWR) in 2015. Getting 65 percent of this group of Americans to manage their high levels of LDL cholesterol by 2017 is one of the major targets of the U.S. Department of Health and Human Services' Million Hearts initiative to prevent one million heart attacks and strokes.

As such, the data indicates that there is no significant improvement in treatment rates from 2011 to present day. In fact, it is expected that the situation may worsen as statins go off brand and generic brands capture market share. With this loss in market share, it cannot be expected that brand name pharmaceutical manufacturers will be able to maintain the level of support for hyperlipidemia that has been provided over the past three decades in terms of scientific, educational, and promotional endeavors. Support for statins via education, science etc. will not come from generic manufacturers. Thus, at present, it is uncertain how the U.S. Department of Health and Human Services' Million Hearts initiative's goals will be accomplished.

Given the above background, what is needed in the art are systems and methods for qualifying a human subject for delivery of a statin pharmaceutical composition over the counter to treat or prevent an atherosclerotic cardiovascular disease, e.g., by lowering cholesterol.

SUMMARY

The present disclosure addresses the need in the art for systems and methods qualifying a human subject for delivery of a statin pharmaceutical composition over the counter to treat or prevent an atherosclerotic cardiovascular disease, e.g., by lowering cholesterol. In the present disclosure, systems and methods are provided for over the counter delivery of a statin to a subject. Survey results from the subject are run against a first plurality of filters. When a filter in the first plurality is fired, the subject is deemed not qualified. The survey results are also run against a second plurality of filters. When a respective filter in the second plurality is fired, the subject is provided with a corresponding warning. The method proceeds to a fulfillment process when no filter in the first plurality fires and the subject has acknowledged each warning associated with each fired filter in the second plurality. The fulfillment stores the composition order, communicates a drug facts label for the statin to the subject, and authorizes, upon subject confirmation that the label has been read, provision of the statin to the subject, the authorization including a destination associated with the subject.

As such, one aspect of the present disclosure provides a computer system for qualifying a human subject for delivery of a statin pharmaceutical composition over the counter to lower cholesterol. The computer system comprises one or more processors and a memory. The memory comprises non-transitory instructions which, when executed by the one or more processor, perform a method. In the method, a first survey of the subject is conducted thereby obtaining a first plurality of survey results.

In some embodiments, the first plurality of survey results comprises a sex of the subject, whether the subject is female and one of (i) pregnant, (ii) breastfeeding, or (iii) planning to become pregnant, whether the subject has or has ever had liver disease, an age of the subject, a total cholesterol level of the subject, an HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications includes cyclosporine, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

All or a portion of the first plurality of survey results are run against a first plurality of filters of a first category class. When a respective filter in the first plurality of filters is fired, the subject is deemed not qualified for delivery of the statin pharmaceutical composition and the method is terminated without delivery of the statin pharmaceutical composition to the subject. In some embodiments, the first plurality of filters comprises a pregnancy filter, a cyclosporine filter, and a liver disease filter.

The method continues by running all or a portion of the first plurality of survey results against a second plurality of filters of a second category class. When a respective filter in the second plurality of filters is fired, the subject is provided with a warning corresponding to the respective filter. In some embodiments, the second plurality of filters comprises a total cholesterol level filter, a pooled cohort equation filter, an age filter, a drug interaction filter, an alcohol consumption filter, an adverse reaction filter, and an atherosclerotic cardiovascular event filter.

In some embodiments, the pooled cohort equation filter incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease. When the risk satisfies a first threshold range or a first threshold value the pooled cohort equation filter is deemed fired.

The method continues by obtaining acknowledgment from the subject for the warning issued to the subject by any filter in the second plurality of filters.

The method continues by proceeding with a fulfillment process when (i) no filter in the first plurality of filters has been fired and (ii) the subject has acknowledged each warning associated with each filter in the second plurality of filters that was fired.

In some embodiments, the fulfillment process comprises storing an indication in a subject profile associated with the subject of an initial order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject, where the authorization includes a destination associated with the subject (e.g., where the statin pharmaceutical composition or what store the statin pharmaceutical composition should be shipped to in order to be picked up by the subject).

In some embodiments, the first plurality of survey results further comprises whether the subject has ever had a kidney disease. In some embodiments, the second plurality of filters of the second category class includes a kidney disease filter.

In some embodiments, the second plurality of filters of the second category class includes an Asian descent filter. In some embodiments, the Asian descent filter is fired when the first plurality of survey results indicates that the subject is Asian.

In some embodiments the atherosclerotic cardiovascular disease is a coronary heart disease (e.g., myocardial infarction, angina, coronary artery stenosis, etc.), a cerebrovascular disease (e.g., transient ischemic attack, ischemic stroke, carotid artery stenosis, etc.), a peripheral artery disease (e.g., claudication), or an aortic atherosclerotic disease (e.g., abdominal aortic aneurysm, secending thoracic aneurysm, etc.).

In some embodiments, the risk for the atherosclerotic cardiovascular disease is a lifetime risk, three year risk, five year risk, ten year risk, or fifteen year risk.

In some embodiments, the pooled cohort equation is implemented as a multivariable Cox proportional hazard regression.

In some embodiments, the statin pharmaceutical composition comprises lovastatin, fluvastatin, atorvastatin, rosuvastatin, simvastatin, pravastatin, or pitavastatin. For instance, in some embodiments the pharmaceutical composition is lovastatin at a daily dosage of between 15 mg and 25 mg. In some embodiments, the pharmaceutical composition is fluvastatin at a daily dosage of between 20 mg and 40 mg. In some embodiments, the pharmaceutical composition is atorvastatin at a daily dosage of between 20 mg and 80 mg. In some embodiments, the pharmaceutical composition is rosuvastatin at a daily dosage of between 2.5 mg and 15 mg. In some embodiments, the pharmaceutical composition is simvastatin at a daily dosage of between 10 mg and 40 mg. In some embodiments, the pharmaceutical composition is pravastatin at a daily dosage of between 10 mg and 80 mg. In some embodiments, the pharmaceutical composition is fluvastatin at a daily dosage of 70 mg-90 mg. In some embodiments, the pharmaceutical composition is pitavastatin at a daily dosage of 1 mg-4 mg.

In some embodiments, the over the counter drug facts label specifies that the statin pharmaceutical composition comprises rosuvastatin and that it is to be taken by the subject at a predetermined dosage per day that is between 4 mg and 15 mg per day.

In some embodiments, the over the counter drug facts label specifies that the statin pharmaceutical composition comprises rosuvastatin and that it is to be taken by the subject at a predetermined dosage per day that is between 4 mg and 11 mg per day.

In some embodiments, the over the counter drug facts label specifies that the statin pharmaceutical composition comprises atorvastatin or simvastatin and that it is to be taken by the subject at a predetermined dosage per day that is between 10 mg and 25 mg per day.

In some embodiments, the provision of the statin pharmaceutical composition to the subject comprises shipping the statin pharmaceutical composition to a physical address associated with the subject. In other embodiments, the provision of the statin pharmaceutical composition to the subject comprises shipping the statin pharmaceutical composition to a pharmacy associated with the subject.

In some embodiments, the first pregnancy filter is fired when the first plurality of survey results indicate that the subject is pregnant.

In some embodiments, the age filter is fired when the first plurality of survey results indicates that the subject is a woman that is aged 49 or less or aged 76 or more.

In some embodiments, the age filter is fired when the first plurality of survey results indicates that the subject is a man that is aged 39 or less or aged 66 or more.

In some embodiments, the liver disease or allergic reaction to the statin pharmaceutical composition filter is fired when the first plurality of survey results indicate that the subject has incurred a liver disease or an allergic reaction to the statin pharmaceutical composition.

In some embodiments, the total cholesterol level filter is fired when the first plurality of survey results indicates that the subject has a total cholesterol of less than 130 mg/dl or greater than 275 mg/dl. In some embodiments, the total cholesterol level filter is fired when the first plurality of survey results indicates that the subject has a total cholesterol of less than 160 mg/dl or greater than 260 mg/dl.

In some embodiments, the risk for the atherosclerotic cardiovascular disease is a 10 year risk and the first threshold value of the pooled cohort equation filter is 7.5 percent. In some embodiments, the risk for the atherosclerotic cardiovascular disease is a 10 year risk, and the first threshold value of the pooled cohort equation filter is 7.5 percent.

In some embodiments, the Asian descent filter is fired when the first plurality of survey results indicates that the subject is Asian. In some embodiments, the Asian descent filter is not used.

In some embodiments, the drug interaction filter is fired when the first plurality of survey results indicates that the subject is presently taking cyclosporine, a blood thinner, warfarin, an HIV/AIDS medication, colchicine, a Hepatitis medication, a cholesterol lowering medication, itraconazole, ketoconazole, or fluconazole. In some embodiments, the drug interaction filter is not used.

In some embodiments, the alcohol filter is fired when the first plurality of survey results indicates that the subject consumes an average of three or more servings of alcohol per day. In some embodiments, the alcohol filter is fired when the first plurality of survey results indicates that the subject consumes an average of two or more servings of alcohol per day. In some embodiments, the alcohol filter is fired when the first plurality of survey results indicates that the subject consumes an average of one or more servings of alcohol per day. In some embodiments, the alcohol filter is fired when the first plurality of survey results indicates that the subject consumes an average of four or more servings of alcohol per day. In some embodiments, the alcohol filter is fired when the first plurality of survey results indicates that the subject consumes an average of five or more servings of alcohol per day. In some embodiments, the alcohol filter is not used.

In some embodiments, the provision of the statin pharmaceutical composition to the subject in the fulfillment process provides the statin pharmaceutical composition at a first predetermined dosage per day when and the risk derived by the pooled cohort equation filter is in a first threshold range, and the provision of the statin pharmaceutical composition to the subject in the fulfillment process provides the statin pharmaceutical composition at a second predetermined dosage per day when and the risk derived by the pooled cohort equation filter is in a second threshold range. As example, in some embodiments the statin pharmaceutical composition comprises rosuvastatin, the risk for the atherosclerotic cardiovascular disease is a 10 year risk, the first threshold range is between 5 percent and 7.5 percent, the first predetermined dosage per day is between 4 mg and 8 mg, the second threshold range is between 7.5 percent and 10 percent, and the second predetermined dosage per day is between 8 mg and 11 mg.

In some embodiments, the method further comprises responsive to receiving a re-order request from the subject for the statin pharmaceutical composition, performing a procedure comprising conducting a second survey of the subject thereby obtaining a second plurality of survey results. The second plurality of survey results comprises whether the subject has experienced muscle irregularity since taking the statin pharmaceutical composition, whether the subject is pregnant, whether the subject is taking a medication that interacts with the statin pharmaceutical composition, and whether the subject had an atherosclerotic cardiovascular event (e.g., heart attack or stroke) or a heart procedure since last ordering the statin pharmaceutical composition. The procedure further comprises running all or a portion of the plurality of second survey results against a third plurality of filters, where, when a respective filter in the third plurality of filters is fired, an action corresponding to the respective filter is triggered, and where the third plurality of filters comprises the pregnancy filter, a muscle irregularity filter, a second drug interaction filter, and an atherosclerotic cardiovascular event filter. The re-fulfillment process further comprises obtaining acknowledgment from the subject for the warning issued to the subject by any filter in the third plurality of filters.

The re-fulfillment process further proceeds when i) the re-fulfillment process is not already terminated by the firing of a filter in the third plurality of filters and (ii) the subject has acknowledged each warning associated with each filter in the third plurality of filters that was fired and that is associated with a warning.

The re-fulfillment process further comprises storing an indication in a subject profile of a re-order for the statin pharmaceutical composition, communicating an over the counter drug facts label for the statin pharmaceutical composition to the subject, and authorizing, upon confirmation from the subject that the over the counter drug facts label has been received and read, a re-order provision of the statin pharmaceutical composition to the subject, where the authorization includes a destination of the subject.

In some embodiments, the muscle irregularity filter is fired when the second plurality of survey results indicates that the subject has experienced an unexplained muscle cramp or weakness since taking the statin pharmaceutical composition, the pregnancy filter is fired when the second plurality of survey results indicate that the subject is pregnant and results in termination of the re-fulfillment procedure, and the second drug interaction filter is fired when the second plurality of survey results indicates that the subject is presently taking cyclosporine, a blood thinner, warfarin, an HIV/AIDS medication, or a cholesterol lowering medication.

Another aspect of the present disclosure provides a method for qualifying a human subject for delivery of a statin pharmaceutical composition over the counter to lower cholesterol. The method comprises conducting a first survey of the subject thereby obtaining a first plurality of survey results. The first plurality of survey results comprises (i) a sex of the subject, whether the subject is female and one of (a) pregnant, (b) breastfeeding, or (c) planning to become pregnant, (iii) whether the subject has or has ever had a liver disease, (iv) an age of the subject, (v) a total cholesterol level of the subject, (vi) a HDL cholesterol count of the subject, (vii) a systolic blood pressure of the subject, (viii) a race of the subject, (ix) whether the subject is taking a high blood pressure medication, (x) whether the subject is taking one or more medications that interact with the statin pharmaceutical composition, where the one or more medications include cyclosporine, (xi) a smoking status of the subject, (xii) a diabetes status of the subject, (xiii) an alcohol consumption status of the subject, (xiv) whether the subject has had an adverse reaction to a cholesterol lowering medication, and (xv) whether the subject has ever had an atherosclerotic cardiovascular event or had a heart procedure. All or a portion of the first plurality of survey results are run against a first plurality of filters of a first category class. When a respective filter in the first plurality of filters is fired, the subject is deemed not qualified for delivery of the statin pharmaceutical composition and the method is terminated without delivery of the statin pharmaceutical composition to the subject. The first plurality of filters comprises a pregnancy filter, a cyclosporine filter, and a liver disease filter. All or a portion of the first plurality of survey results are also run against a second plurality of filters of a second category class. When a respective filter in the second plurality of filters is fired, the subject is provided with a warning corresponding to the respective filter. The second plurality of filters comprises a total cholesterol level filter, a pooled cohort equation filter that incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value, the pooled cohort equation filter is deemed fired. The second plurality of filters further comprises an age filter, a drug interaction filter, an alcohol consumption filter, an adverse reaction filter, and an atherosclerotic cardiovascular event filter. Acknowledgment is obtained from the subject for the warning issued to the subject by any filter in the second plurality of filters. The method proceeds with a fulfillment process when (i) no filter in the first plurality of filters has been fired and (ii) the subject has acknowledged each warning associated with each filter in the second plurality of filters that was fired. the fulfillment process comprises storing an indication in a subject profile of an initial order for the statin pharmaceutical composition, communicating an over the counter drug facts label for the statin pharmaceutical composition to the subject, and authorizing, upon confirmation from the subject that the over the counter drug facts label has been received and read, provision of the statin pharmaceutical composition to the subject, where the authorization includes a destination associated with the subject.

Another aspect of the present disclosure provides a non-transitory computer readable storage medium, where the non-transitory computer readable storage medium stores instructions, which when executed by a computer system, cause a computer system to perform any of the methods for qualifying a human subject for delivery of a statin pharmaceutical composition over the counter to lower cholesterol disclosed herein.

BRIEF DESCRIPTION OF THE DRAWINGS

FIGS. 4A, 4B, 4C, 4D, and 4E, collectively provide a flow chart of processes for qualifying a human subject for delivery of a statin pharmaceutical composition over the counter to lower cholesterol, where elements in dashed boxes are optional, in accordance with various embodiments of the present disclosure.

FIGS. 5A, 5B, 5C, 5D, 5E, 5F, 5G, 5H, 5I, 5J, 5K, 5L, 5M, 5N, 5O, 5P, 5Q, 5R, 5S, 5T, 5U, and 5V collectively illustrates a first survey of a subject for obtaining a first plurality of survey results in accordance with an embodiment of the present disclosure.

FIG. 6 illustrates feedback from a first survey in accordance with an embodiment of the present disclosure.

FIG. 7 illustrates assessment results from a first survey in accordance with an embodiment of the present disclosure.

FIG. 8 illustrates a comparison of contraindications for various statin pharmaceutical agents.

Like reference numerals refer to corresponding parts throughout the several views of the drawings.

DETAILED DESCRIPTION

The present disclosure conducts a survey of a subject to obtain survey results in order to determine if the subject qualifies for an over the counter (OTC) statin pharmaceutical composition for the treatment or prevention of an atherosclerotic cardiovascular disease. The survey results are used as the basis for running filters of a first category class. If the triggering conditions of any of the filters in the first category class are fired, the subject does not qualify for the OTC statin pharmaceutical composition. The survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired a fulfillment process is initiated for OTC delivery of the statin pharmaceutical composition to a destination associated with the subject.

Figure 1:
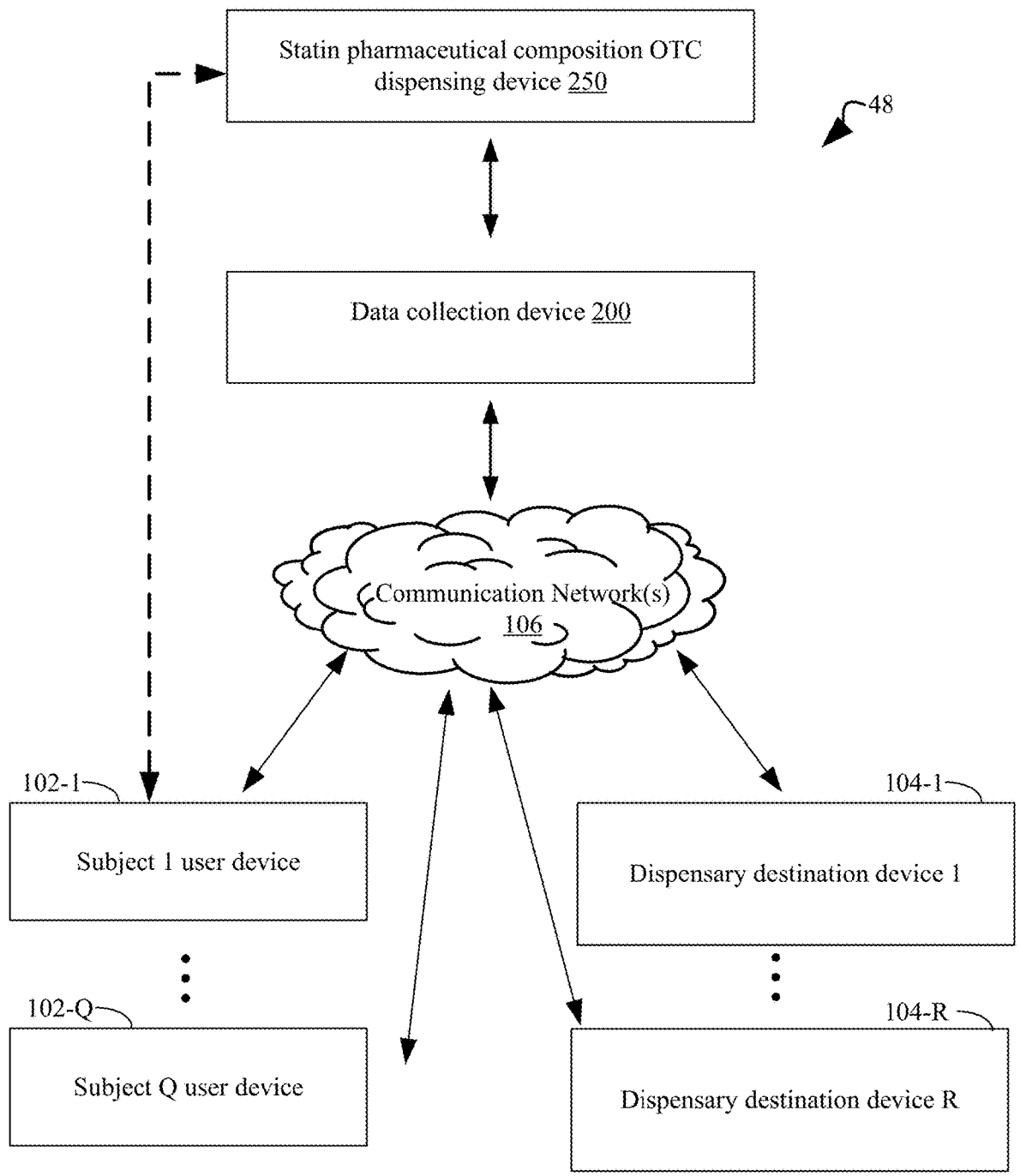
FIG. 1 illustrates an exemplary system topology that includes a statin pharmaceutical composition over the counter (OTC) dispensing device for qualifying a human subject for delivery of a statin pharmaceutical composition over the counter to lower cholesterol, a data collection device for collecting subject data, one or more user devices associated with human subjects, and one or more dispensary destinations for distributing the statin pharmaceutical composition over the counter, where the above-identified components are interconnected, optionally through a communications network, in accordance with an embodiment of the present disclosure.

FIG. 1 illustrates an example of an integrated system 48 for conducting survey of subjects in order to qualifying them for OTC delivery of a statin pharmaceutical composition and for delivery of the statin pharmaceutical composition to the destinations associated with qualifying subjects. The integrated system 48 includes one or more connected user devices 102 for entering survey data and making requests for the statin pharmaceutical composition, one or more dispensary destination devices 104 that receive instructions to provide the statin pharmaceutical composition to qualifying subjects, a statin pharmaceutical composition over the counter (OTC) dispensing device 250 and one or more data collection devices 200 for collecting subject data. Throughout the present disclosure, the data collection device 200 and the statin pharmaceutical composition OTC dispensing device 250 will be referenced as separate devices solely for purposes of clarity. That is, the disclosed functionality of the data collection device 200 and the disclosed functionality of the statin pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the statin pharmaceutical composition OTC dispensing device 250 are contained in a single device.

With the integrated system 48, survey results from the subjects are run against a first plurality of filters. When a filter in the first plurality of filters is fired for a respective subject, the respective subject is deemed not qualified. The survey results are also run against a second plurality of filters. When a respective filter in the second plurality is fired for a respective subject, the respective subject is provided with a warning associated with the respective filter. The method enabled by the integrated system 48 proceeds to a fulfillment process when no filter in the first plurality fires and the subject has acknowledged or otherwise successfully addressed each warning associated with each filter in the second plurality of filters that fired. As part of the fulfillment process, the composition order is stored (e.g., in a user profile associated with the subject to receive the drug), a drug facts label for the statin is communicated to the qualifying subject, and upon subject confirmation that the label has been read, authorization is granted to dispense the statin to the subject at a particular destination associated with the subject.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over the counter" means to provide by retail purchase, subject to the constraints disclosed herein, but without a prescription or license from a physician or medical practitioner.

As used herein, the term "contraindication" refers to a condition that makes a treatment, e.g., over the counter use of a statin pharmaceutical agent, inadvisable. Contraindications include physical characteristics of a subject, e.g., pregnancy or liver disease, and contemporaneous drug use, e.g., cyclosporine use. In the present context, identification of a contraindication fires a filter of a first category class, which prevents authorizing provision of a statin pharmaceutical composition, in accordance with some implementations of the methods, systems, and software disclosed herein.

As used herein, the term "risk factor" refers to a condition that makes a treatment, e.g., over the counter use of a statin pharmaceutical agent, possibly inadvisable. Risk factors include physical characteristics of a subject, e.g., a cholesterol level, and contemporaneous drug use, e.g., use of a blood thinner. In the present context, identification of a risk factor fires a filter of a second category class, which prevents authorizing provision of a statin pharmaceutical composition without confirmation that the subject has discussed the risk factor with a medical professional, in accordance with some implementations of the methods, systems, and software disclosed herein.

In the context of the present disclosure, classification of a condition as either a contraindication or a risk factor is specific to a particular identity and dose of a statin pharmaceutical composition being authorized for over the counter use. Classification of a particular condition, e.g., contemporaneous cyclosporine use, may vary between different statin pharmaceutical compositions (e.g., it may be classified as a contraindication for a first statin, a risk factor for a second statin, and/or neither for a third statin). Likewise, a particular condition may be classified as a contraindication for use of a particular statin at a first over the counter dosage, classified as a risk factor for the same particular statin at a second (e.g., lower) over the counter dosage, and/or classified as neither for the same particular statin at a third (e.g., lowest) over the counter dosage).

Referring to FIG. 1, the statin pharmaceutical composition OTC dispensing device 250 qualifies a human subject for delivery of a statin pharmaceutical composition over the counter to lower cholesterol. To do this, the data collection device 200, which is in electrical communication with the statin pharmaceutical composition OTC dispensing device 250, receives survey results originating from one or more user devices 102 associated with subjects. In some embodiments, the data collection device 200 receives such survey results directly from the user devices 102. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the statin pharmaceutical composition OTC dispensing device 250.

In some embodiments, the data collection device 200 and/or the statin pharmaceutical composition OTC dispensing device 250 is not proximate to the subject and/or does not have wireless capabilities or such wireless capabilities are not used for the purpose of acquiring survey results. In such embodiments, a communication network 106 may be used to survey questions from the statin pharmaceutical composition OTC dispensing device 250 to user devices 102 and the answers to such survey questions from the user devices 102 to the data collection device 200 and/or the statin pharmaceutical composition OTC dispensing device 250. Further, in some embodiments, the communication network 106 is used to communicate authorization to dispense the statin survey questions from the statin pharmaceutical composition OTC dispensing device 250 to dispensary destination devices 104.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoW), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the statin pharmaceutical composition OTC dispensing device 250. Further, the data collection device 200 and/or the statin pharmaceutical composition OTC dispensing device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Figure 2:
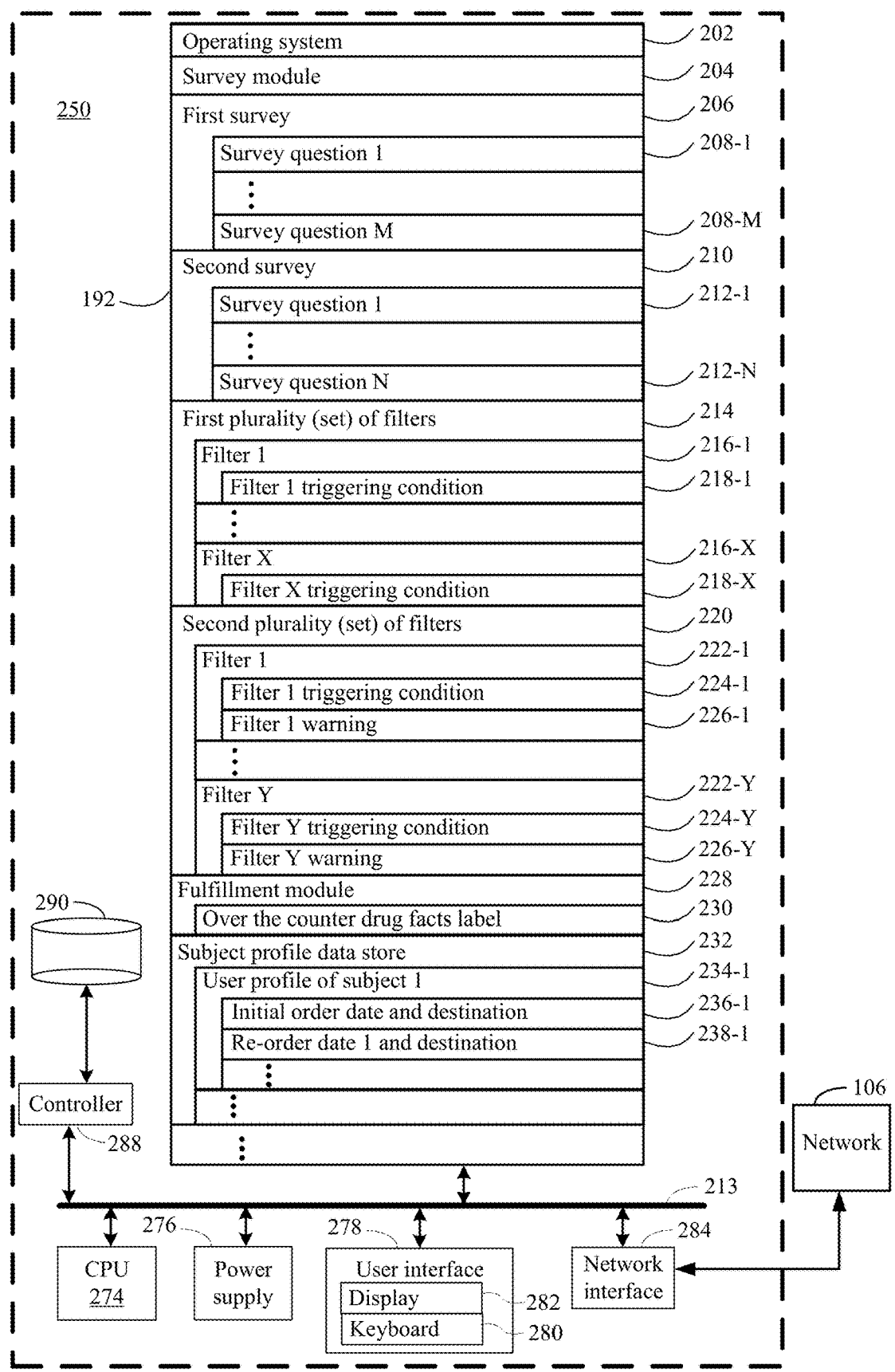
FIG. 2 illustrates an example device for qualifying a human subject for delivery of a statin pharmaceutical composition over the counter to lower cholesterol in accordance with an embodiment of the present disclosure.

Referring to FIG. 2, in typical embodiments, the statin pharmaceutical composition OTC dispensing device 250 comprises one or more computers. For purposes of illustration in FIG. 2, the statin pharmaceutical composition OTC dispensing device 250 is represented as a single computer that includes all of the functionality for qualifying a human subject for delivery of a statin pharmaceutical composition over the counter to lower cholesterol. However, the disclosure is not so limited. In some embodiments, the functionality for qualifying a human subject for delivery of a statin pharmaceutical composition over the counter to lower cholesterol is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary statin pharmaceutical composition OTC dispensing device 250 for optimizing a timing of a short acting insulin medicament dosage in a prescribed insulin regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the statin pharmaceutical composition OTC dispensing device 250 but that can be electronically accessed by the statin pharmaceutical composition OTC dispensing device 250 over an Internet, intranet, or other form of network or electronic cable (illustrated as element 106 in FIG. 2) using network interface 284.

In some embodiments, the memory 192 of the statin pharmaceutical composition OTC dispensing device 250 for optimizing a timing of a short acting insulin medicament dosage in a prescribed insulin regimen for a subject comprises and stores:

an operating system 202 that includes procedures for handling various basic system services;
a survey module 204;
a first survey 206 for qualifying a subject for an initial of a statin pharmaceutical composition over the counter to treat or prevent an atherosclerotic cardiovascular disease, e.g., by lowering cholesterol, the first survey comprising a first plurality of survey questions 208;
a second survey 210 for qualifying a subject for a re-order of the statin pharmaceutical composition, second survey comprising a second plurality of survey questions 212;
a first plurality of filters 214 of a first category class, each respective filter 216 in the first plurality of filters comprising one or more filter triggering conditions 218;
a second plurality of filters 220 of a second category class, each respective filter 222 in the second plurality of filters comprising one or more filter triggering conditions 224 and one or more associated filter warnings 226;
a fulfillment module 228 for executing a fulfillment process when (i) no filter 216 in the first plurality of filters 214 has been fired for a subject and (ii) the subject has acknowledged each warning associated with each filter 224 in the second plurality of filters 220 that was fired as a result of answers by the subject to the first survey 206 or the second survey 208, where the fulfillment process comprises communicating an over the counter drug facts label 230 for the statin pharmaceutical composition to the subject and receiving confirmation from the subject that the over the counter drug facts label has been received and read; and
a subject profile data store 232 comprising a user profile 234 for each of a plurality of subjects, each respective user profile 234 including information about a corresponding subject in the plurality of subjects including an initial order date and destination 236 and any re-order date and the destination 238 for the statin pharmaceutical composition made by the corresponding subject using the statin pharmaceutical composition OTC dispensing device 250.

In some embodiments, the survey module 204 is accessible within any browser (phone, tablet, laptop/desktop). In some embodiments the survey 204 runs on native device frameworks, and is available for download onto a user device 102 running an operating system 102 such as Android or iOS.

In some implementations, one or more of the above identified data elements or modules of the statin pharmaceutical composition OTC dispensing device 250 for qualifying a human subject for delivery of a statin pharmaceutical composition over the counter to lower cholesterol are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a statin pharmaceutical composition OTC dispensing device 250 for qualifying a human subject for delivery of a statin pharmaceutical composition over the counter to lower cholesterol is a smart phone (e.g., an iPHONE), laptop, tablet computer, desktop computer, or other form of electronic device (e.g., a gaming console). In some embodiments, the statin pharmaceutical composition OTC dispensing device 250 is not mobile. In some embodiments, the statin pharmaceutical composition OTC dispensing device 250 is mobile.

In some embodiments, the statin pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the statin pharmaceutical composition OTC dispensing device 250 are shown in FIG. 2 in order to better emphasize the additional software modules that are installed on the statin pharmaceutical composition OTC dispensing device 250.

Figure 3:
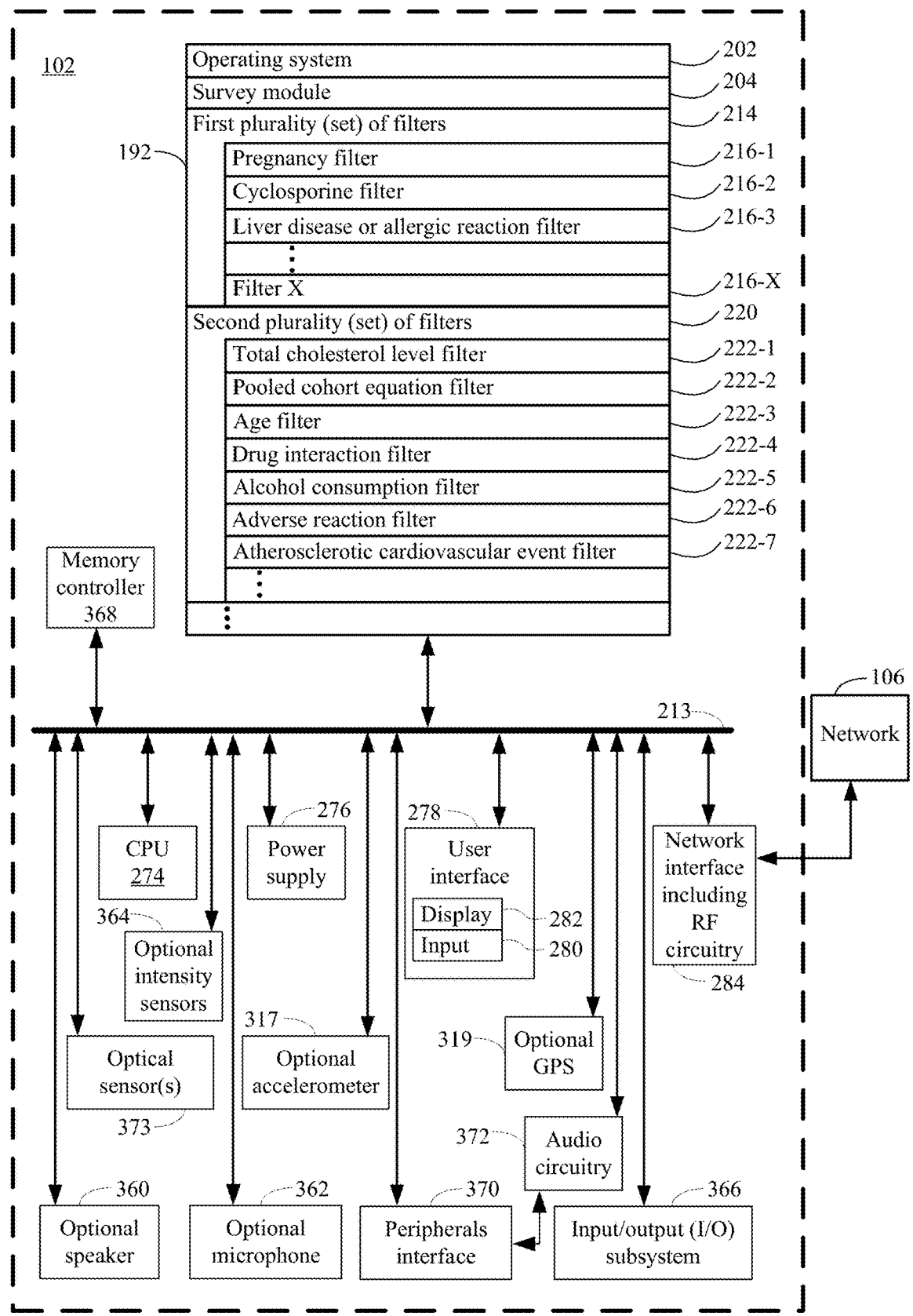
FIG. 3 illustrates an example device associated with a human subject for qualifying the human subject for delivery of a statin pharmaceutical composition over the counter to lower cholesterol in accordance with an embodiment of the present disclosure.

FIG. 3 provides a description of a user device 102 that can be used with the instant disclosure. The user device 102 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 282 of the user device 102), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey in order to qualify for delivery of a statin pharmaceutical composition over the counter to lower cholesterol, and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the statin pharmaceutical composition OTC dispensing device 250, such as CPU(s) 274 is, optionally, controlled by the memory controller 368.

In some embodiments, the memory 192 of the user device 102 illustrated in FIG. 3 optionally includes the survey module 204 described above in conjunction with the statin pharmaceutical composition OTC dispensing device 250. Moreover, in some embodiments, as illustrated in FIG. 3, the first plurality of filters 214 comprises a pregnancy filter 216-1, a cyclosporine filter 216-2, and a liver disease or allergic reaction to the statin pharmaceutical composition filter 216-3. Also, in some embodiments, as further illustrated in FIG. 3, the second plurality of filters 220 comprises a total cholesterol level filter 222-1, a pooled cohort equation filter 222-2, an age filter 222-3, a drug interaction filter 222-4, an alcohol consumption filter 222-5, an adverse reaction filter 222-6, and an atherosclerotic cardiovascular event filter 222-7.

In some embodiments, the optional accelerometer 317, optional GPS 319, and/or magnetometer (not shown) of the user device 102 or such components are used to recommend to qualifying subjects one or more suitable destinations for delivery of the statin pharmaceutical composition over the counter.

The peripherals interface 370 can be used to couple input and output peripherals of the device to CPU(s) 274 and memory 192. The one or more processors 274 run or execute various software programs and/or sets of instructions stored in memory 192, such as the survey module 204, to perform various functions for the user device 102 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the survey module 204, survey questions 208/212, answers to survey questions 208/212, and/or the over the counter drug facts label 230 are communicated using this RF circuitry. In some embodiments, the RF circuitry 108 converts electrical signals to/from electromagnetic signals and communicates with communications networks and other communications devices and/or the data collection device 200 and/or the statin pharmaceutical composition OTC dispensing device 250 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 282 on the front of the user device 102, so that the input 280 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for delivery of a statin pharmaceutical composition over the counter to lower cholesterol), to help diagnose a subject's condition remotely, or to acquire visual physiological measurements of the subject, etc.).

As illustrated in FIG. 3, the user device 102 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the user device 102 is a smart phone. In other embodiments, the user device 102 is not a smart phone but rather is a tablet computer, desktop computer, emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with electronic medical records to exchange information in any way.

Now that details of a system 48 for qualifying a human subject for delivery of a statin pharmaceutical composition over the counter to lower cholesterol have been disclosed, details regarding a flow chart of processes and features of the system, in accordance with an embodiment of the present disclosure, are disclosed with reference to FIGS. 4A through 4E. In some embodiments, such processes and features of the system are carried out by the survey module 204 illustrated in FIGS. 2 and 3 and/or the fulfillment module 228 illustrated in FIG. 3. In some embodiments, the fulfillment module 228 and the survey module 204 are a single software module.

Blocks 402-406. With reference to block 402 of FIG. 4A, the goal of the present disclosure is to qualify subjects for delivery of a statin pharmaceutical composition over the counter to lower cholesterol using a computer system such as a statin pharmaceutical composition OTC dispensing device 250. As illustrated in FIG. 2, the statin pharmaceutical composition OTC dispensing device 250 comprises one or more processors 274 and a memory 192/290. The memory stores non-transitory instructions that, when executed by the one or more processors, perform a method.

In some embodiments, the statin pharmaceutical composition comprises atorvastatin (LIPITOR®), fluvastatin (LESCOL®, LESCOL XL®), lovastatin (ALTOPREV®), pitavastatin (LIVALO®), pravastatin (PRAVACHOL®), rosuvastatin (CRESTOR®), or simvastatin (ZOCOR®) (404). These statin pharmaceutical compositions are described in Lee et al., 2007, "Comparison of Efficacy and Tolerability of Pitavastatin and Atorvastatin: an 8-Week, Multicenter, Randomized, Open-Label, Dose-Titration Study in Korean Patients with Hypercholesterolemia," Clin Ther. 2007; 29:2365-73; Bradford et al., 1990, "Expanded clinical evaluation of lovastatin (EXCEL) study design and patient characteristics of a double blind, placebo controlled study in patients with moderate hypercholesterolemia. American Journal of Cardiology 66: p. 44B-55B; Serruys et al., 2002, "Fluvastatin for Prevention of Cardiac Events Following Successful First Percutaneous Coronary Intervention: A Randomized Controlled Trial.," JAMA 287:p. 3215-3222; Sacks et al. 1996, "The effect of pravastatin on coronary events after myocardial infarction in patients with average cholesterol levels. Cholesterol and Recurrent Events Trial investigators," New England Journal of Medicine, 1996. 335(14): p. 001-9; *Anonymous,* 2002 "Heart Protection Study Collaborative Group, MRC/BHF Heart Protection Study of cholesterol lowering with simvastatin in 20,536 high-risk individuals: a randomised placebo-controlled trial," Lancet 360: p. 7-22; Jones et al., 2003, "Comparison of the efficacy and safety of rosuvastatin versus atorvastatin, simvastatin, and pravastatin across doses (STELLAR Trial)," Am J Cardiol. 92 (2): 152-60 each of which is hereby incorporated by reference. In some embodiments, the statin pharmaceutical composition comprises a statin and another lipid-lowering drug, such as Atorvastatin/Ezetimibe (LIPTRUZET®)), Lovastatin+Niacin (ADVICOR®), Simvastatin/Ezetimibe (VYTORIN®), or Simvastatin/Niacin-ER (SIMCOR®)).

In some embodiments, the statin pharmaceutical composition comprises any compound described by any of claims 1-117 of U.S. Pat. No. 5,969,156 C1, entitled "CRYSTALLINE [R-(R*,R*)]-2-(4-DFLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID HEMI CALCIUM SALT (ATORVASTATIN)," which is hereby incorporated by reference. In some embodiments, the statin pharmaceutical composition comprises any compound disclosed in U.S. Pat. No. 5,969,156 C1, entitled "CRYSTALLINE [R-(R*,R*)]-2-(4-DFLUOROPHENYL)-β,δ-DIHYDROXY-5-(1-METHYLETHYL)-3-PHENYL-4-[(PHENYLAMINO) CARBONYL]-1H-PYRROLE-1-HEPTANOIC ACID HEMI CALCIUM SALT (ATORVASTATIN)," which is hereby incorporated by reference.

In some embodiments, the statin pharmaceutical composition comprises any compound described by any of claims 1-20 of U.S. Pat. No. 6,242,003 B1, entitled "Organic Compounds," which is hereby incorporated by reference. In some embodiments, the statin pharmaceutical composition comprises any compound disclosed in U.S. Pat. No. 6,242,003 B1, entitled "Organic Compounds," which is hereby incorporated by reference.

In some embodiments, the statin pharmaceutical composition comprises any compound disclosed in U.S. Pat. Nos. 5,854,259; 5,586,336; 6,465,477; 7,022,713; and/or 8,557,993 each of which is hereby incorporated by reference.

In some embodiments, the statin pharmaceutical composition comprises any compound disclosed in U.S. Pat. Nos. 6,316,460; 6,858,618; 7,030,152; 7,964,614; and/or RE37314, each of which is hereby incorporated by reference.

It will be appreciated that the survey questions and filters applied to the survey answers may vary depending upon the statin pharmaceutical composition being distributed. This is due to differences in the contra-indication profiles of the various statins, e.g., due to different drug-drug interactions, routes of drug clearance, etc. of the different statins. For example, co-administration of 500 mg Tipranavir/200 mg BID causes a 9.4-fold increase in atorvastatin (LIPITOR®) AUC and 8.6-fold increase in Cmax, but only a 1.4-fold and 2.2-fold increases in rosuvastatin (CRESTOR®) AUC and Cmax, respectively. As such, in some embodiments, a survey qualifying a subject for OTC use of atorvastatin may ask whether the subject is currently taking Tipranavir and BID, while a survey qualifying a subject for OTC use of rosuvastatin may not.

A comparison of some contraindications for prescription use of several statin pharmaceutical agents is presented in FIG. 8. The list of contraindications in FIG. 8 is non-exhaustive. The skilled artisan may know of other contraindications for a particular statin pharmaceutical agent and/or treat risk factors as contraindications dependent upon the intended use of the statin pharmaceutical agent.

For example, concurrent use of a cyclosporine pharmaceutical agent is not a contraindication for prescription use of rosuvastatin (e.g., CRESTOR), although there is a known drug-drug interaction. This may be because the medical professional prescribing the rosuvastatin can evaluate the risk and/or severity of the drug-drug interaction in the particular patient at the prescribed dosages. However, in some embodiments, concurrent use of a cyclosporine pharmaceutical agent is treated as a contraindication for OTC use of rosuvastatin (e.g., a subject's response to whether they are currently taking a cyclosporine pharmaceutical agent is applied to a type 1 filter, which prevents authorization for dispensing OTC rosuvastatin when fired).

Likewise, in some embodiments, contraindications for use of a prescription-strength pharmaceutical agent are treated only as risk factors, or not at all, when qualifying a subject for a lower-dose OTC use of a statin pharmaceutical agent. For example, in some embodiments, where the OTC dosage of a lovastatin pharmaceutical agent (e.g., MEVACOR) is sufficiently low as to negate severe drug-drug interactions with strong CYP3A4 inhibitors, concurrent use of a CYP3A4 pharmaceutical agent is treated only as a risk factor (e.g., a subject's response to whether they are currently taking a strong CYP3A4 inhibitor is applied to a type 2 filter, which prompts the subject to confer with their physician about possible drug-drug interactions and requires confirmation that the subject consulted with their physician prior to allowing authorization for dispensing OTC lovastatin when fired).

Referring to block 406, in some embodiments, the atherosclerotic cardiovascular disease is a coronary heart disease such as a myocardial infarction, angina, or coronary artery stenosis. In some embodiments, the atherosclerotic cardiovascular disease is a cerebrovascular disease such as a transient ischemic attack, an ischemic stroke, or carotid artery stenosis. In some embodiments, the atherosclerotic cardiovascular disease is a peripheral artery disease such as claudication. In some embodiments, the atherosclerotic cardiovascular disease is an aortic atherosclerotic disease such as an abdominal aortic aneurysm, or a secending thoracic aneurysm.

Figure 5A:
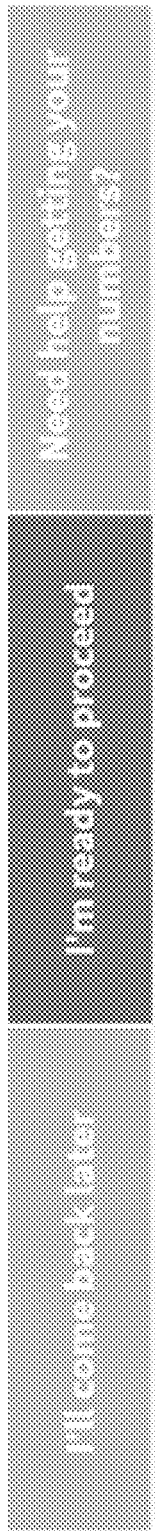

Blocks 408-410. Referring to block 408 of FIG. 4A, in the method a first survey 206 of the subject is conducted thereby obtaining a first plurality of survey results to survey questions. In some embodiments, the first survey 206 of the subject is initiated with a message such as the one illustrated in FIG. 5A. Referring to block 410, in some embodiments, the first plurality of survey results includes a sex of the subject (e.g., responsive to a survey question 208 such as the one illustrated in FIG. 5G), whether the subject is female and one of (i) pregnant, (ii) breastfeeding, or (iii) planning to become pregnant (e.g., responsive to a survey question 208 such as the one illustrated in FIG. 5B), whether the subject has or has ever had a liver disease (e.g., responsive to a survey question 208 such as the one illustrated in FIG. 5C and the accompanying information of FIG. 5D), an age of the subject (e.g., responsive to a survey question 208 such as the one illustrated in FIG. 5H), a total cholesterol level of the subject (e.g., responsive to a survey question 208 such as the one illustrated in FIG. 5J), a high-density lipoprotein (HDL) count of the subject (e.g., responsive to a survey question 208 such as the one illustrated in FIG. 5K), a systolic blood pressure of the subject (e.g., responsive to a survey question 208 such as the one illustrated in FIG. 5L), a race of the subject (e.g., responsive to a survey question 208 such as the one illustrated in FIG. 5I), whether the subject is taking a high blood pressure medication (e.g., responsive to a survey question 208 such as the one illustrated in FIG. 5M and the accompanying information of FIG. 5N), whether the subject is taking one or more medications that interact with the statin pharmaceutical composition, where the one or more medications include cyclosporine (e.g., responsive to a survey question 208 such as the one illustrated in FIG. 5E and accompanying information of FIG. 5F, and/or responsive to a survey question 208 such as the one illustrated in FIG. 5T with the accompanying information of FIG. 5U), a smoking status of the subject (e.g., responsive to a survey question 208 such as the one illustrated in FIG. 5P), a diabetes status of the subject (e.g., responsive to a survey question 208 such as the one illustrated in FIG. 5O), an alcohol consumption status of the subject (e.g., responsive to a survey question 208 such as the one illustrated in FIG. 5R), whether the subject has had an adverse reaction to a cholesterol lowering medication (e.g., responsive to a survey question 208 such as the one illustrated in FIG. 5S), and whether the subject has ever had an atherosclerotic cardiovascular event or had a heart procedure (e.g., responsive to a survey question 208 such as the one illustrated in FIG. 5V).

Blocks 412-416. Referring to block 412 of FIG. 4A, once the first survey 206 has been completed by a prospective subject thereby obtaining a first plurality of survey results, all or a portion of the first plurality of survey results are run against a first plurality of filters 214 of a first category class. When a respective filter 216 in the first plurality of filters 214 is fired, the subject is deemed not qualified for delivery of the statin pharmaceutical composition and the method is terminated without delivery of the statin pharmaceutical composition to the subject. Blocks 414 and 416 illustrate specific filters in the first plurality of filters and their exemplary triggering conditions that cause them to fire.

Referring to block 414, in some embodiments, the first plurality of filters 214 comprises a pregnancy filter. Referring to block 416, the pregnancy filter is fired when the first plurality of survey results indicate that the subject is pregnant. In some embodiments, the pregnancy filter is fired when the first plurality of survey results indicate that the subject is pregnant, is thinking of becoming pregnant, is breastfeeding, or plans to become pregnant, in line with the survey question 208 illustrated in FIG. 5B. If the pregnancy filter is fired, the subject is not permitted to obtain the statin pharmaceutical composition over the counter.

In some embodiments, the first plurality of filters 214 comprises a cyclosporine filter. In some embodiments, the cyclosporine filter is fired when the first plurality of survey results indicate that the subject is taking cyclosporine in line with the survey question 208 illustrated in FIG. 5E and accompanying information of FIG. 5F. If the cyclosporine filter is fired, the subject is not permitted to obtain the statin pharmaceutical composition over the counter.

In some embodiments, the first plurality of filters 214 comprises a liver disease or allergic reaction to a statin pharmaceutical composition filter. In some embodiments, the liver disease or allergic reaction to the statin pharmaceutical composition filter is fired when the first plurality of survey results indicate that the subject has incurred a liver disease or an allergic reaction to any cholesterol lowering medication in line with the survey question 208 illustrated in FIGS. 5C and 5S, respectfully.

Blocks 418-438. Referring to block 418 of FIG. 4B, if none of the first plurality of filters are fired, the method continues with the running of all or a portion of the first plurality of survey results against a second plurality of filters 220 of a second category class. When a respective filter 222 in the second plurality of filters is fired, the subject is provided with a warning 226 corresponding to the respective filter.

For example, referring to block 420 and FIG. 3, in some embodiments, the second plurality of filters 220 comprises a total cholesterol level filter 222-1, an age filter 222-3, a drug interaction filter 222-4, an alcohol consumption filter 222-5, an adverse reaction filter 222-6, an atherosclerotic cardiovascular event filter 222-7, and/or a pooled cohort equation filter 222-2.

The pooled cohort equation filter incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease. Referring to block 422, when the risk satisfies a first threshold range or a first threshold value the pooled cohort equation filter 222-2 is deemed fired. Referring to block 424, in some embodiments, the risk for the atherosclerotic cardiovascular disease used in calculating the pooled cohort equation is a lifetime risk, a five year risk, or a 10 year risk. Referring to block 426, in some embodiments, the pooled cohort equation is implemented as a multivariable Cox proportional hazard regression. Referring to block 428, in some embodiments, the risk for the atherosclerotic cardiovascular disease used in calculating the pooled cohort equation is a 10 year risk, and the first threshold value is 7.5 percent.

The pooled cohort equations estimate the probability of incurring a hard atherosclerotic cardiovascular disease (AS-CVD) event in a given time period, such as in the next 5 years, the next 10 years, or in a subject's lifetime. In some embodiments, the pooled cohort equation for the pooled cohort equation filter 222-2 is calculated using the guidelines set forth in Goff D C Jr, Lloyd-Jones D M, Bennett G, Coady S, D'Agostino R B Sr, Gibbons R, Greenland P, Lackland D T, Levy D, O'Donnell C J, Robinson J, Schwartz J S, Smith S C Jr, Sorlie P, Shero S T, Stone N J, Wilson P W. 2013 ACC/AHA guideline on the assessment of cardiovascular risk: a report of the American College of Cardiology/American Heart Association Task Force on Practice Guidelines. Circulation. 2013; 00:000-000, which is hereby incorporated by reference. Following Goff Id., calculation of the 10-year risk estimate for a hard ASCVD event using the pooled cohort equations is done as a series of steps. The natural log of the subject's age, total cholesterol, HDL-C, and systolic blood pressure are first calculated with the systolic blood pressure being either a treated or untreated value. For example, calculation of the pooled cohort equations estimate the probability of a Caucasian male subject 55 years of age with total cholesterol 213 mg/dL, HDL-C 50 mg/dL, untreated systolic BP 120 mm Hg, nonsmoker, and without diabetes determine the probability of a hard ASCVD event in the next 10 years using Goff Id. begins by first taking the natural log of the subject's age (4.01), the natural log of the subject's total cholesterol (5.36), the natural log of the subject's HDL-C (3.91), and the natural log of the subject's systolic blood pressure (4.79). These values are then multiplied by the coefficients from the equation ("Coefficient" column of Table A of Goff Id.) for the specific race-sex group of the individual to obtain "coefficient×values." That is:

multiply the natural log of the subject's age (4.01) by the coefficient 12.344 to obtain the "coefficient×value" of 49.47, multiply the natural log of the subject's total cholesterol (5.36) by the coefficient 11.853 to obtain the "coefficient×value" of 63.55, multiply the natural log of the subject's HDL-C (3.91) by the coefficient −7.990 to obtain the "coefficient×value" of −31.26, and multiply the natural log of the subject's systolic blood pressure (4.79) by the coefficient 1.764 to obtain the "coefficient x value" of 8.45.

Any appropriate interaction terms are also calculated. Following Goff Id., in the case of the Caucasian male subject 55 years of age, the interaction terms are:

the Log Age (4.01)×Log total Cholesterol (5.36) multiplied by the coefficient −2.664 to obtain the "coefficient x value" of −57.24 and Log Age (4.01)×Log HDL-C (3.91) multiplied by the coefficient 1.769 to obtain the "coefficient×value" of 27.73.

The sum of these "coefficient×value" is then calculated for the individual (49.47+63.55−31.26+8.45−57.24+27.73=60.69). The estimated 10-year risk of a first hard ASCVD event is formally calculated as 1 minus the baseline survival rate at 10 years for the sex/race (in this example Caucasian male), raised to the power of the exponent of the "Coefficient×Value" sum calculated above minus the race (Caucasian) and sex (Male) specific overall mean "Coefficient×Value" sum; or, in equation form:

$$1 - 0.9144 e^{(60.69 - 61.18)}$$

where the number 0.9144 is the baseline survival rate at 10 years for Caucasian males from Goff Id., the number 60.69 is the "coefficient×value" calculated for the particular subject as detailed above, and the number 61.18 is the race (Caucasian) and sex (Male) specific overall mean "Coefficient×Value" from Goff Id. This equates to a 5.3% probability of a first hard ASCVD event within 10 years.

Figure 5B:
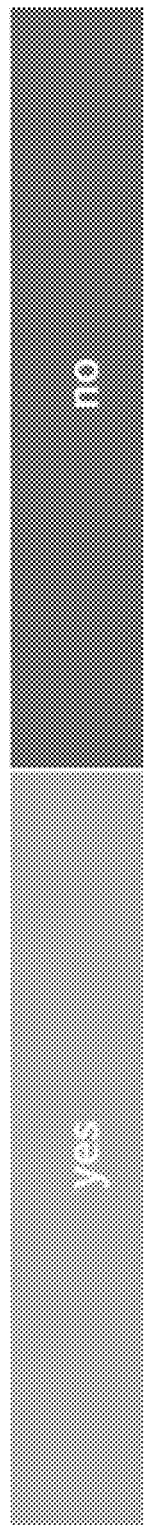
Figure 5C:
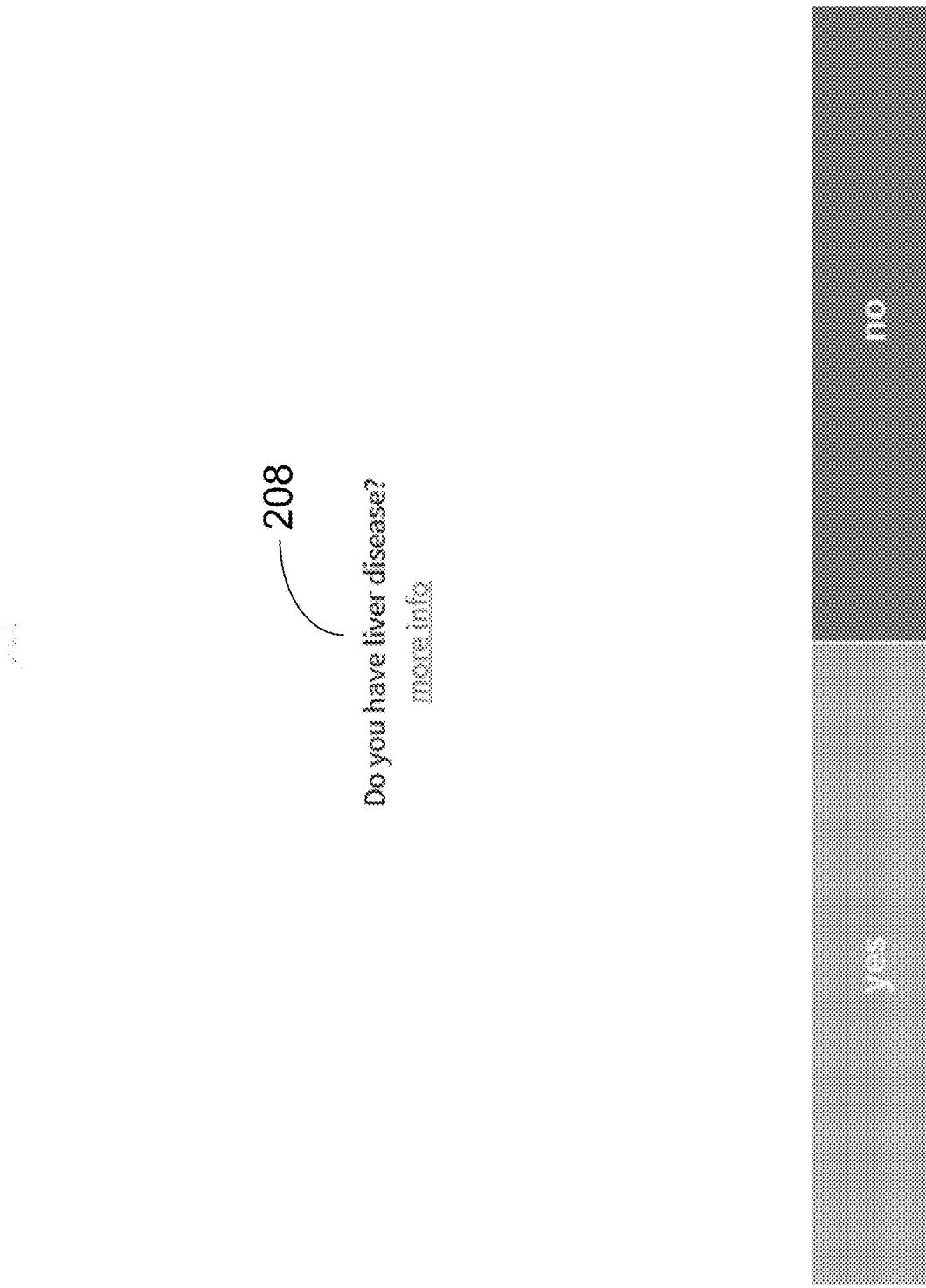
Figure 5D:
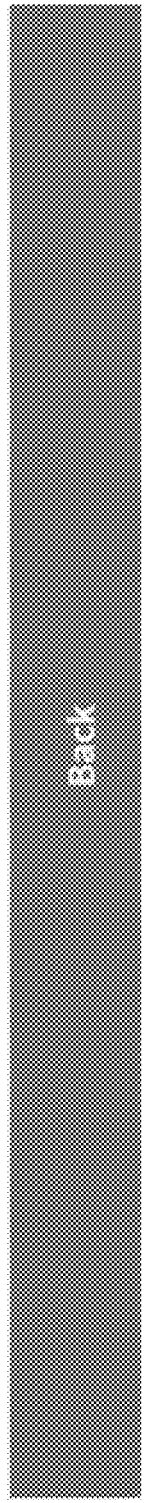
Figure 5E:
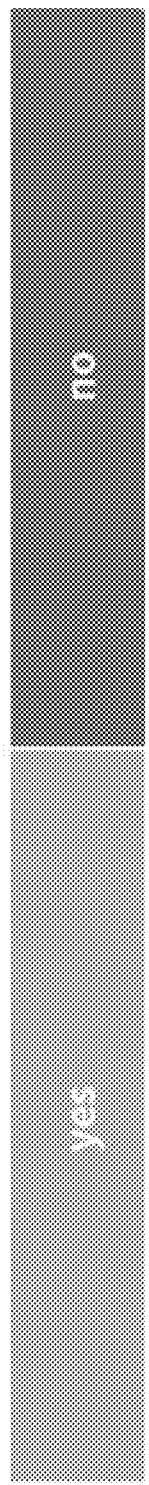
Figure 5F:
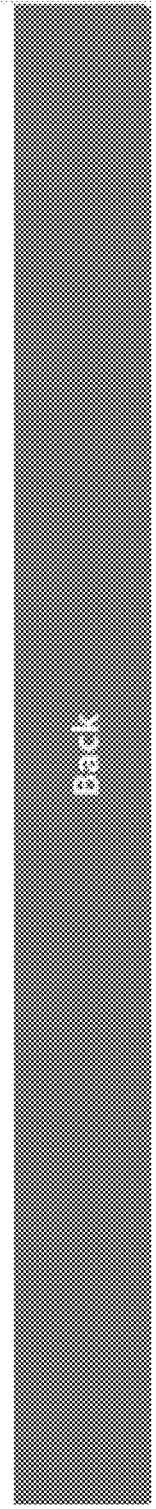
Figure 5G:
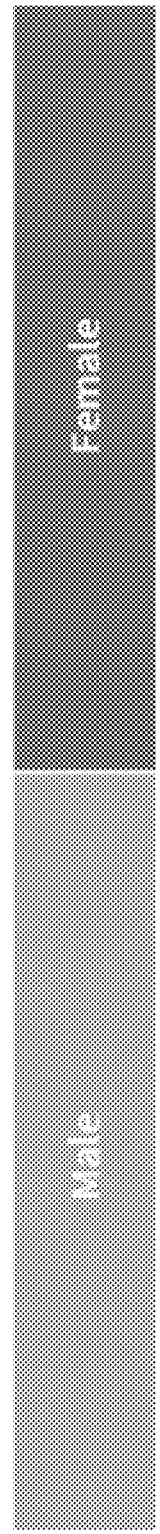
Figure 5K:
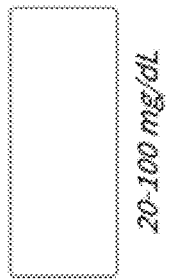
Figure 5M:
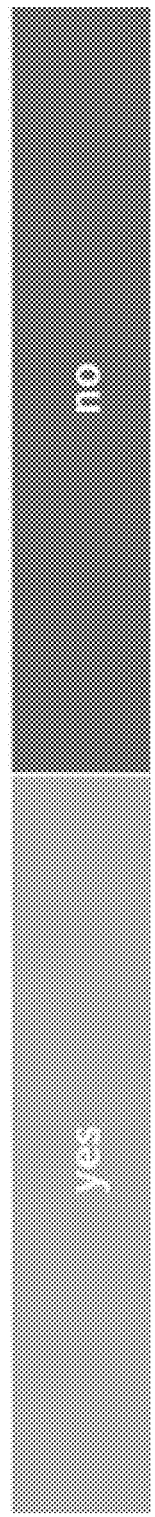
Figure 5N:
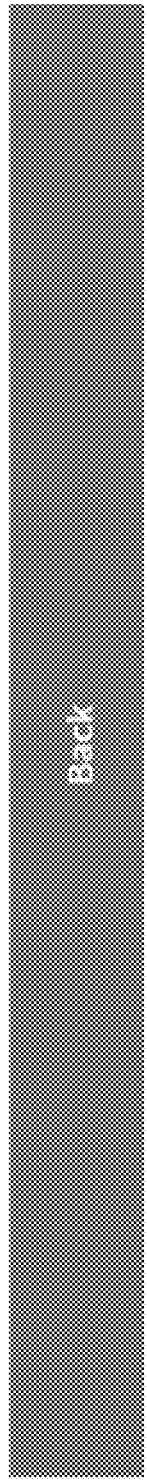
Figure 5P:
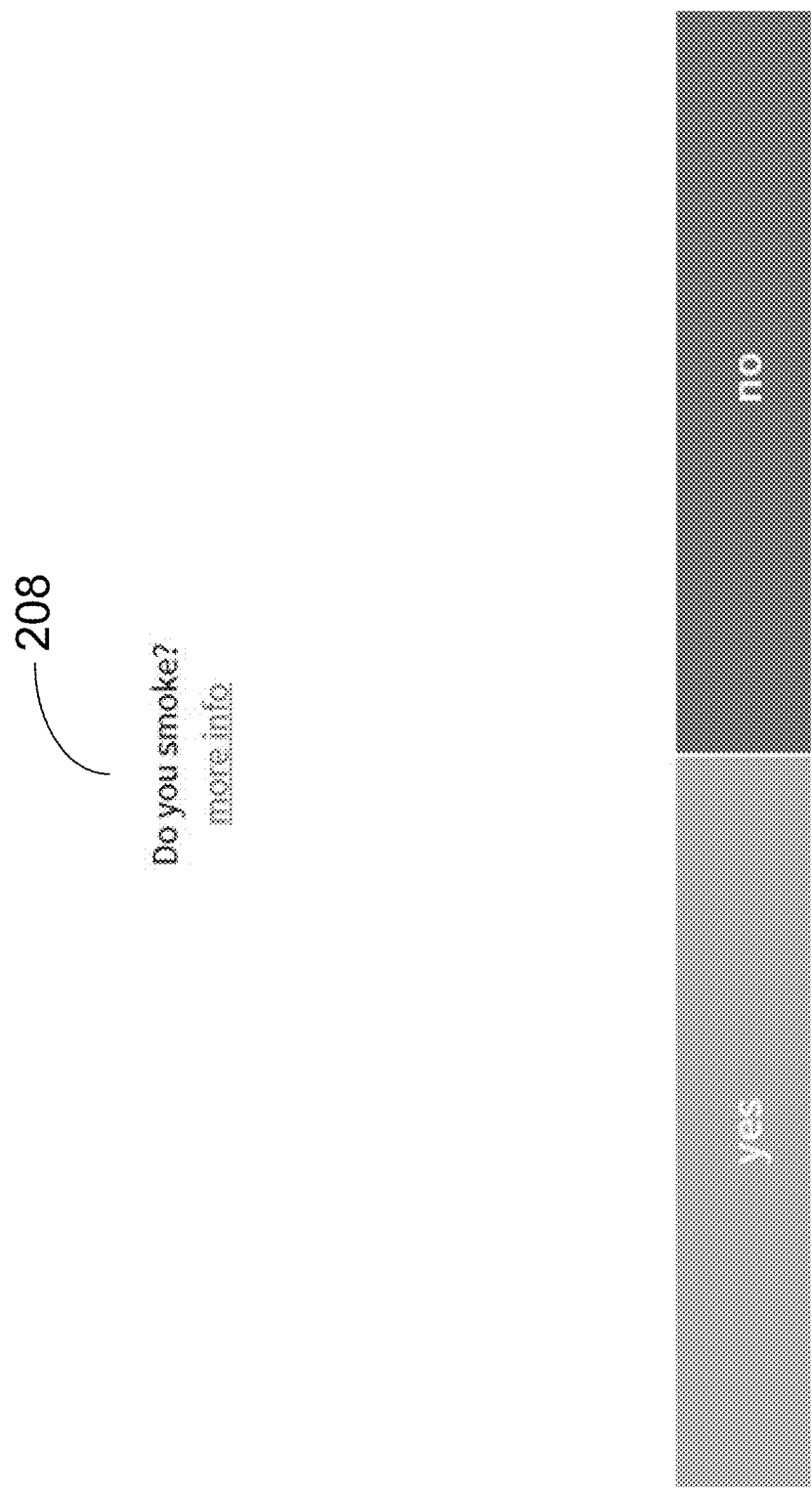

Referring to block 430 of FIG. 5B, in some embodiments the risk for the atherosclerotic cardiovascular disease is a 10 year risk and the first threshold value of the pooled cohort equation filter is 7.5 percent. In such embodiments, if the pooled cohort equation (e.g., the equations and tables set forth in Goff Id. indicate there is a probability of a first hard ASCVD event within 10 years that is less than 7.5 percent, the pooled cohort equation filter 222-2 is fired. When the pooled cohort equation filter 222-2 is fired, the filter warning 226 associated with the pooled cohort equation filter 222-2 is delivered to the subject. Such a warning is illustrated in FIG. 6. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

In some embodiments the risk for the atherosclerotic cardiovascular disease is a 5 year risk, 10 year risk, life time risk, and the first threshold value of the pooled cohort equation filter is 4.0 percent, 4.5 percent, 5.0 percent, 5.5 percent, 6.0 percent, 6.5 percent, 7.0 percent, 7.5 percent, 8.0 percent, 8.5 percent, 9.0 percent, 9.5 percent or 10.0 percent. In such embodiments, if the pooled cohort equation (e.g., the equations and tables set forth in Goff Id. indicate there is a probability of a first hard ASCVD event within the designated time that is less than the first threshold value, the pooled cohort equation filter 222-2 is fired. When the pooled cohort equation filter 222-2 is fired, the filter warning 226 associated with the pooled cohort equation filter 222-2 is delivered to the subject. Such a warning is illustrated in FIG. 6. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

In some embodiments, the total cholesterol level filter 222-1 is fired when the first plurality of survey results indicates that the subject has a total cholesterol of less than 130 mg/dl or greater than 275 mg/dl. When the total cholesterol level filter 222-1 is fired, the filter warning 226 associated with the total cholesterol level filter 222-1 is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

In some embodiments, the total cholesterol level filter 222-1 is fired when the first plurality of survey results indicates that the subject has a total cholesterol of less than 100 mg/dl, less than 110 mg/dl, less than 115 mg/dl, less than 120 mg/dl, less than 125 mg/dl, less than 130 mg/dl, less than 135 mg/dl or greater than 250 mg/dl, greater than 255 mg/dl, greater than 260 mg/dl, greater than 265 mg/dl, greater than 270 mg/dl, greater than 275 mg/dl, greater than 280 mg/dl, greater than 285 mg/dl, greater than 290 mg/dl, greater than 295 mg/dl or greater than 300 mg/dl. When the total cholesterol level filter 222-1 is fired, the filter warning 226 associated with the total cholesterol level filter 222-1 is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

In some embodiments, the age filter 222-3 is fired when the first plurality of survey results indicates that the subject is a woman that is aged 49 or less or aged 76 or more, and the age filter is fired when the first plurality of survey results indicates that the subject is a man that is aged 39 or less or aged 66 or more. When the age filter 222-3 is fired, the filter warning 226 associated with the age filter 222-3 is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

In some embodiments, the age filter 222-3 is fired when the first plurality of survey results indicates that the subject is a woman that is aged 44 or less, 45 or less, 46, or less, 47 or less, 48 or less, or 49 or less or aged 70 or more, 71 or more, 72 or more, 73 or more, 74 or more, 75 or more or 76 or more, and the age filter is fired when the first plurality of survey results indicates that the subject is a man that is aged 35 or less, 36 or less, 37 or less, 38 or less or 39 or less or aged 61 or more, 62, or more, 63 or more, 64 or more, 65 or more, 66 or more, 67 or more, 68 or more, 69 or more, 70 or more, 71 or more, or 72 or more. In such embodiments, when the age filter 222-3 is fired, the filter warning 226 associated with the age filter 222-3 is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

Referring to block 432 of FIG. 4B, in some embodiments the drug interaction filter 222-4 is fired when the first plurality of survey results indicates that the subject is presently taking a blood thinner, warfarin, an HIV/AIDS medication, colchicine, a Hepatitis medication, a cholesterol lowering medication, itraconazole, ketoconazole, or fluconazole. When the drug interaction filter 222-4 is fired, the filter warning 226 associated with the drug interaction filter 222-4 is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

Inclusion of a drug within drug interaction filter 222-4 is dependent upon the identity and/or the dosage of the statin pharmaceutical composition being authorized for over the counter use. In some implementations, a drug that interacts with a statin pharmaceutical composition is included within a filter in the first plurality of filters 214, rather than within drug interaction filter 222-4 of the second plurality of filters 220. For example, according to some implementations, a particular drug (e.g., itraconazole or strong CYP3A4 inhibitors generally) is included in drug-interaction filter 222-4 (e.g., as a risk factor) for a first statin pharmaceutical composition (e.g., rosuvastatin) but included in a filter in the first plurality of filters 214 (e.g., as a contraindication) for a second statin pharmaceutical composition (e.g., simvastatin).

FIG. 8 includes a table of contraindications, including several contraindicated drug-drug interactions, for several prescription pharmaceutical statin compositions. However, a person skilled in the art will know whether to include a certain drug within drug interaction filter 222-4 or as a separate filter in the first plurality of filters 214, based on the severity and risk of the drug interaction with the particular identity and dosage of the statin being authorized for over the counter use.

In some embodiments, the alcohol consumption filter 222-5 filter is fired when the first plurality of survey results indicates that the subject consumes an average of three or more servings of alcohol per day. When the alcohol consumption filter 222-5 filter is fired, the filter warning 226 associated with the alcohol consumption filter 222-5 filter is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

In some embodiments, the alcohol consumption filter 222-5 filter is fired when the first plurality of survey results indicates that the subject consumes an average of four or more servings of alcohol per week, an average of five or more servings of alcohol per week, an average of six or more servings of alcohol per week, an average of one or more servings of alcohol per day, an average of two or more servings of alcohol per day, an average of three or more servings of alcohol per day, or an average of four or more servings of alcohol per day, or an average of five or more servings of alcohol per day. In such embodiments, when the alcohol consumption filter 222-5 filter is fired, the filter warning 226 associated with the alcohol consumption filter 222-5 filter is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

Figure 5Q:
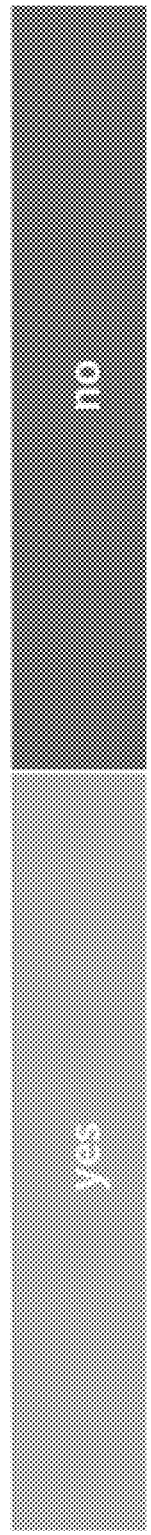
Figure 5R:
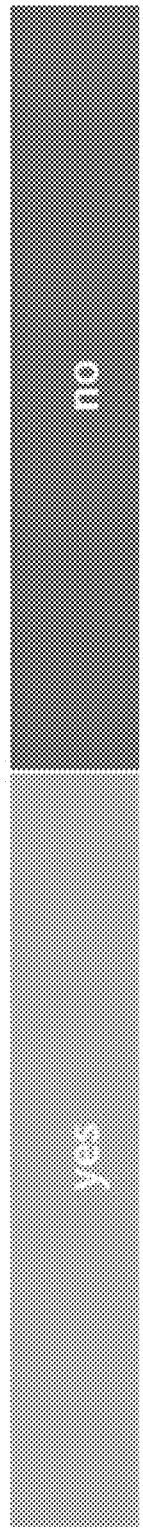
Figure 5S:
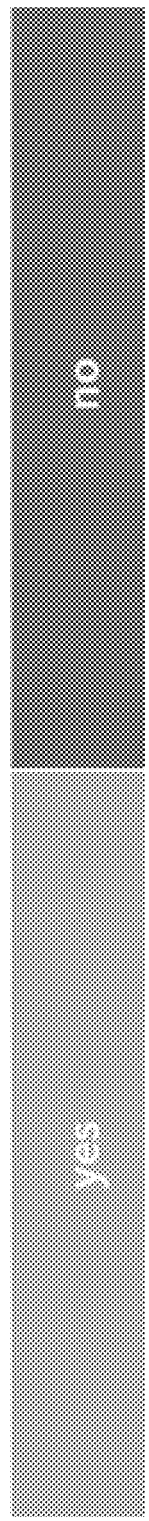
Figure 5T:
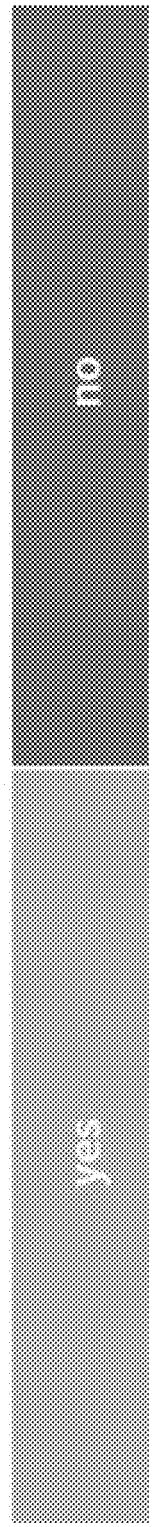
Figure 5U:
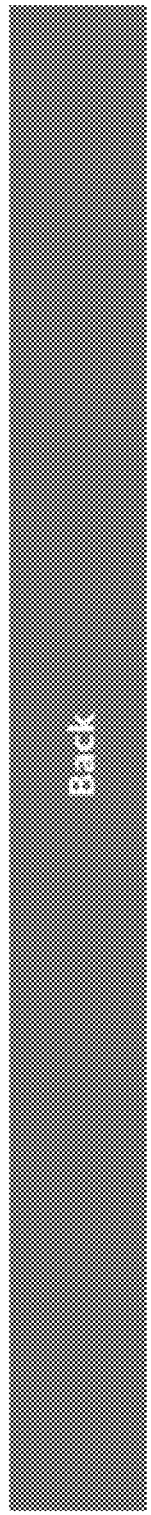
Figure 5V:
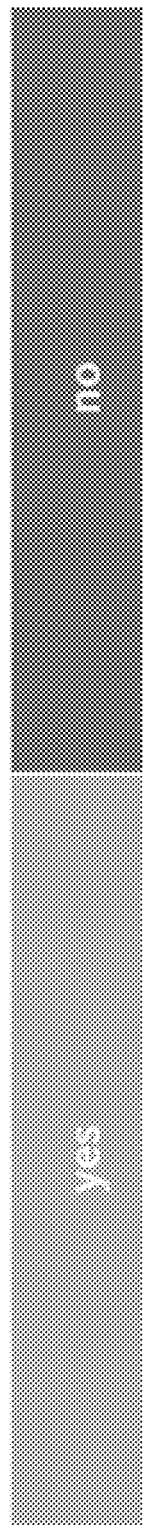

Referring to block 434, in some embodiments, the first plurality of survey results includes whether the subject has had a kidney disease (e.g., responsive to a survey question 208 such as the one illustrated in FIG. 5Q), and the second plurality of filters includes a kidney disease filter (block 434). In such embodiments, when the kidney disease filter is fired, the filter warning 226 associated with the kidney disease filter is delivered to the subject. If the subject indicates that they have spoken to their doctor and the doctor says that is it ok to take the statin pharmaceutical composition, then process control will proceed with the fulfillment process discussed below with respect to blocks 442-458 provided that the requirements of any other fired filters are satisfied by the subject.

Referring to block 436 of FIG. 4C, in some embodiments, the second plurality of filters includes an Asian decent filter. In such embodiments, the Asian descent filter is fired when the first plurality of survey results indicates that the subject is Asian (block 438).

Referring to block 440 of FIG. 4C, process control continues by obtaining acknowledgment from the subject for any warning issued to the subject by any filter in the second plurality of filters 220. If a filter in the first plurality of filters 214 fires, the subject is denied access to the over the counter statin pharmaceutical composition.

Blocks 442-458. Referring to block 442 of FIG. 4C, as discussed above, process control proceeds to the fulfillment process when (i) no filter in the first plurality of filters 214 has been fired and (ii) the subject has acknowledged each warning associated with each filter in the second plurality of filters that was fired.

Referring to block 444 of FIG. 4C, in some embodiments, the fulfillment process comprises storing an indication in a subject profile 234 of an initial order for the statin pharmaceutical composition.

The fulfillment process further comprises communicating an over the counter drug facts label 230 for the statin pharmaceutical composition to the subject. In some embodiments, the over the counter drug facts label specifies what the statin pharmaceutical composition is for and any risks associated with taking the statin pharmaceutical composition. For instance, in some embodiments, the over the counter drug facts label 230 specifies that the statin pharmaceutical composition comprises rosuvastatin and that it is to be taken by the subject at a predetermined dosage per day that is between 2.5 mg and 15 mg per day (block 446). In another example embodiment, the over the counter drug facts label 230 specifies that the statin pharmaceutical composition comprises rosuvastatin and that it is to be taken by the subject at a predetermined dosage per day that is between 4 mg and 11 mg per day (block 448). In still another example embodiment, the over the counter drug facts label 230 specifies that the statin pharmaceutical composition comprises atorvastatin or simvastatin and that it is to be taken by the subject at a predetermined dosage per day that is between 10 mg and 25 mg per day (block 450).

Figure 4A:
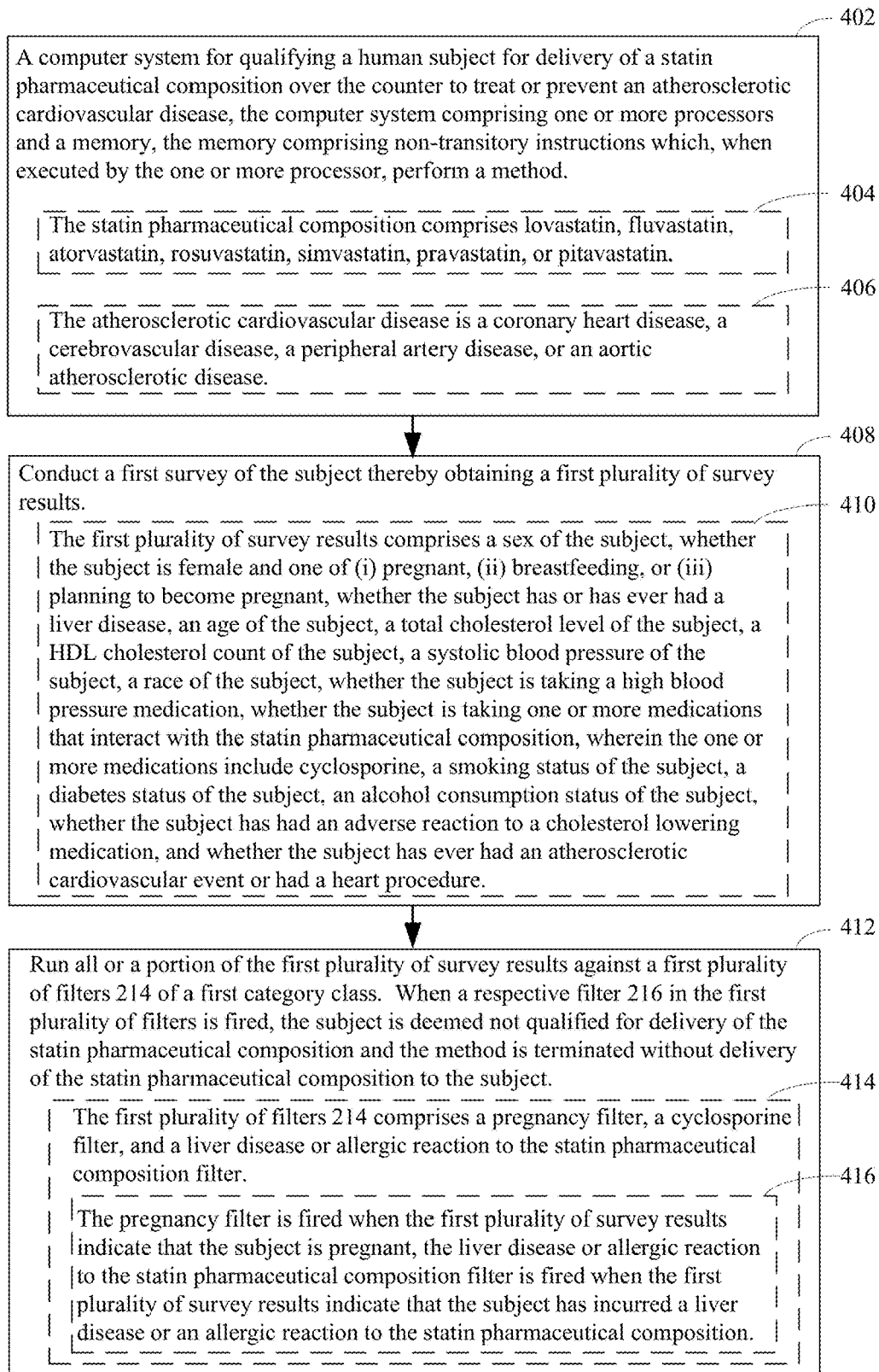
Figure 4D:
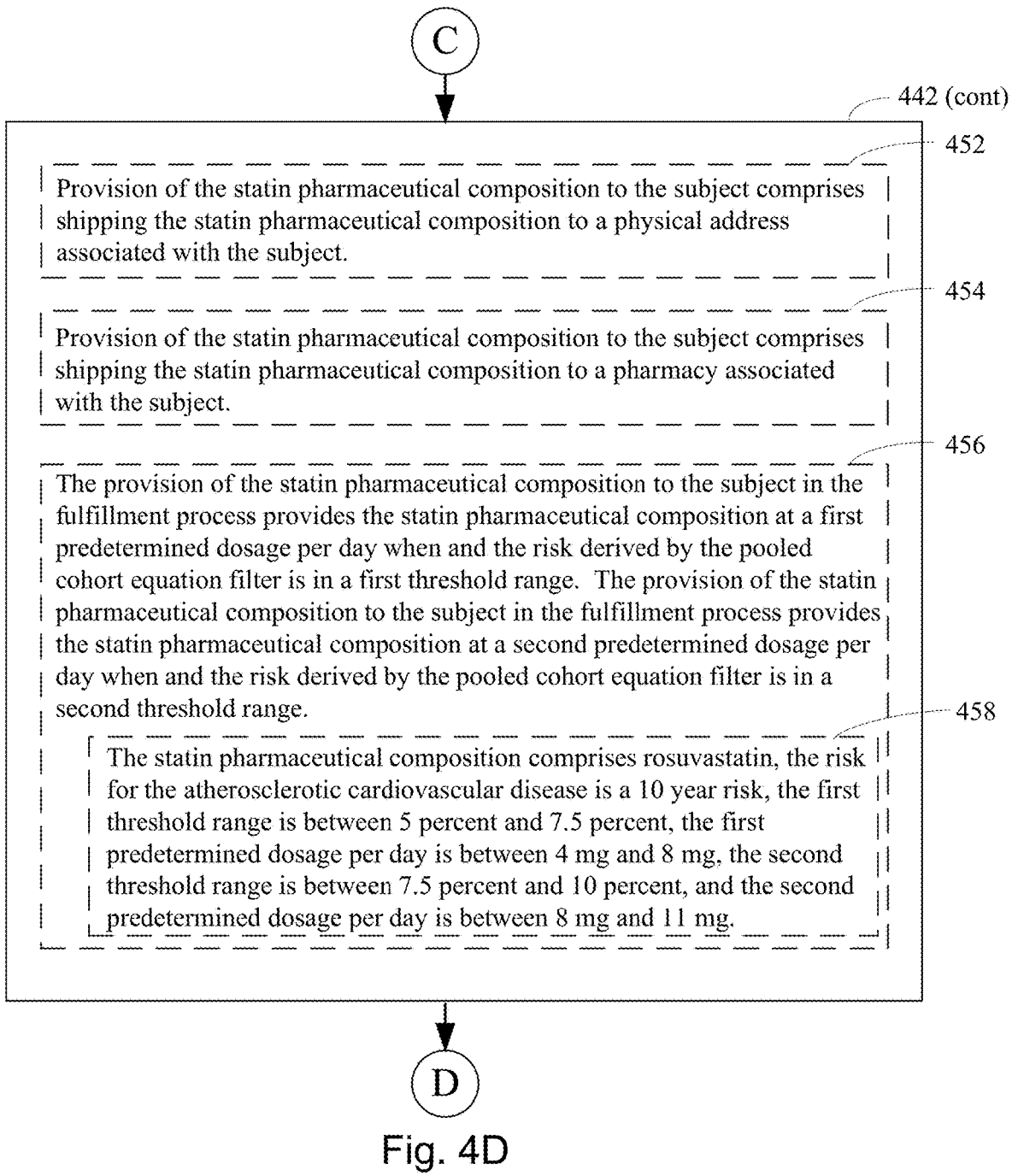

Referring again to block 444 of FIG. 4C, the fulfillment process further comprises authorizing, upon confirmation from the subject that the over the counter drug facts label 230 has been received and read by the subject, provision of the statin pharmaceutical composition to the subject. This authorization includes a destination associated with the subject. In some embodiments, the provision of the statin pharmaceutical composition to the subject comprises shipping the statin pharmaceutical composition to a physical address associated with the subject (block 452). In some embodiments, the provision of the statin pharmaceutical composition to the subject comprises shipping the statin pharmaceutical composition to a pharmacy associated with the subject (block 454). In some embodiments, the provision of the statin pharmaceutical composition to the subject in the fulfillment process provides the statin pharmaceutical composition at a first predetermined dosage per day when and the risk derived by the pooled cohort equation filter 222-2 is in a first threshold range. The provision of the statin pharmaceutical composition to the subject in the fulfillment process provides the statin pharmaceutical composition at a second predetermined dosage per day when and the risk derived by the pooled cohort equation filter 222-2 is in a second threshold range (block 456). Block 458 of FIG. 4D illustrates an example of such an embodiment. In accordance with the example illustrated by block 458, the statin pharmaceutical composition comprises rosuvastatin and the risk for the atherosclerotic cardiovascular disease is a 10 year risk. Thus, what is evaluated by the pooled cohort equation filter 222-2 is the risk of a first hard ASCVD event occurring in the next 10 years. In the example illustrated by block 458, the first threshold range is between 5 percent and 7.5 percent. This means that if the pooled cohort equation filter 222-2 determines that the risk of a first hard ASCVD event occurring in the next 10 years is between 5 percent and 7.5 percent, the first predetermined dosage per day is authorized for the subject (e.g., between 4 mg and 8 mg in the example of block 458). Further, the second threshold range is between 7.5 percent and 10 percent. This means that if the pooled cohort equation filter 222-2 determines that the risk of a first hard ASCVD event occurring in the next 10 years is between 7.5 percent and 10 percent, the second predetermined dosage per day is authorized for the subject (e.g., between 8 mg and 11 mg in the example of block 458).

Blocks 460-462 (re-order). Referring to block 460 of FIG. 4E, responsive to receiving a re-order request from the subject for the statin pharmaceutical composition, a procedure is performed. The procedure comprises (i) conducting a second survey of the subject thereby obtaining a second plurality of survey results. The second plurality of survey results comprises: querying whether the subject has experienced a muscle irregularity since taking the statin pharmaceutical composition, querying whether the subject is pregnant, querying whether the subject is taking a medication that interacts with the statin pharmaceutical composition, and querying whether the subject had an atherosclerotic cardiovascular event or a heart procedure since last ordering the statin pharmaceutical composition. The reordering procedure further comprises running all or a portion of the second plurality of survey results against a third plurality of filters of the second category class. When a respective filter in the third plurality of filters is fired, the subject is provided with a warning corresponding to the respective filter.

In some embodiments, the third plurality of filters comprises the pregnancy filter 216-1 described above in relation to blocks 412 and 414. As was the case for blocks 412 and 414 in the case of the initial survey, when the second plurality of survey results indicate that the subject is pregnant, the pregnancy filter is fired and results in termination of the re-fulfillment procedure.

In some embodiments, the third plurality of filters comprises a muscle irregularity filter. Referring to block 462, in some embodiments, the muscle irregularity filter is fired when the second plurality of survey results indicates that the subject has experienced an unexplained muscle cramp or weakness since taking the statin pharmaceutical composition. When the muscle irregularity filter is fired, the subject is issued a warning regarding muscle irregularities and asked to consult a physician.

In some embodiments, the third plurality of filters comprises a second drug interaction filter. In some embodiments, the second drug interaction filter is fired when the second plurality of survey results indicates that the subject is presently taking cyclosporine, a blood thinner, warfarin, an HIV/AIDS medication, or a cholesterol lowering medication. When the muscle irregularity filter is fired, the subject is issued a warning regarding adverse drug interactions with the statin pharmaceutical composition and asked to consult a physician.

In some embodiments, the third plurality of filters comprises an atherosclerotic cardiovascular event filter 227-7 as described above in relation to block 420. When the atherosclerotic cardiovascular event filter 227-7 is fired, the subject is issued a warning regarding atherosclerotic cardiovascular events and asked to consult a physician.

The procedure further comprises obtaining, when the re-fulfillment process is not terminated, acknowledgment from the subject for each warning issued to the subject by any filter in the third plurality of filters, except the pregnancy filter which results in termination of the re-fulfillment process. The procedure further comprises proceeding with the re-fulfillment process when (i) the re-fulfillment process is not already terminated by the firing of a filter in the third plurality of filters (e.g., the pregnancy filter) and (ii) the subject has acknowledged each warning associated with each filter in the third plurality of filters that was fired and that is associated with a warning (e.g., the muscle irregularity filter, the second drug interaction filter, and/or muscle irregularity filter, etc.).

The re-fulfillment process further comprises storing an indication in a subject profile 234 of a re-order 238 for the statin pharmaceutical composition. The re-fulfillment process further comprises communicating an over the counter drug facts label 230 for the statin pharmaceutical composition to the subject. The re-fulfillment process further comprises authorizing, upon confirmation from the subject that the over the counter drug facts label 230 has been received and read, a re-order provision of the statin pharmaceutical composition to the subject. This re-order provision includes a destination of the subject.

EXAMPLES

Example 1

A computer system is prepared for qualifying a human subject for delivery of a rosuvastatin pharmaceutical composition (e.g., low-dose CRESTOR) over the counter to treat or prevent an atherosclerotic cardiovascular disease (e.g., by lowering cholesterol). The computer system includes instructions for conducting a survey of the subject, to obtain one or more of: a sex of the subject, whether the subject is female and one of (i) pregnant, (ii) breastfeeding, or (iii) planning to become pregnant, whether the subject has or has ever had a liver disease, an age of the subject, a total cholesterol level of the subject, a HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications include cyclosporine, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

The computer system runs survey results against a first series of filters that each prevents authorization for delivery of the OTC statin where the subject's survey results identify a contraindication for the OTC statin. In some embodiments, the first series of filters includes one or more of: a pregnancy filter, a liver disease or allergic reaction to the statin pharmaceutical composition filter, and an optional cyclosporine filter.

The computer system runs survey results against a second series of filters that each generates a warning where the subject's survey results identify a risk factor for the OTC statin. In some embodiments, the first series of filters includes one or more of: a total cholesterol level filter, a pooled cohort equation filter that incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value the pooled cohort equation filter is deemed fired, an age filter, a drug interaction filter, an alcohol consumption filter, an adverse reaction filter, an atherosclerotic cardiovascular event filter, and an optional cyclosporine filter (e.g., when not included in the first series of filters).

The computer system then prompts the subject to acknowledge or deny having discussed these warnings with a medical professional (e.g., their physician). The computer system then proceeds with a fulfillment process only when (i) none of the first series of filters was fired (ii) the subject acknowledged that they discussed each warning issued in association with the second series of filters that was fired.

The computer system stores an indication of an initial order of the OTC statin in a subject profile, and communicates an over the counter drug facts label for the statin pharmaceutical composition to the subject. Upon confirmation from the subject that they have received and read the over the counter drug facts label, the computer system authorizes provision of the OTC statin pharmaceutical composition to the subject.

Example 2

A computer system is prepared for qualifying a human subject for delivery of an atorvastatin pharmaceutical composition (e.g., low-dose LIPITOR) over the counter to treat or prevent an atherosclerotic cardiovascular disease (e.g., by lowering cholesterol). The computer system includes instructions for conducting a survey of the subject, to obtain one or more of: a sex of the subject, whether the subject is female and one of (i) pregnant, (ii) breastfeeding, or (iii) planning to become pregnant, whether the subject has or has ever had a liver disease, an age of the subject, a total cholesterol level of the subject, a HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications include cyclosporine, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

The computer system runs survey results against a first series of filters that each prevents authorization for delivery of the OTC statin where the subject's survey results identify a contraindication for the OTC statin. In some embodiments, the first series of filters includes one or more of: a pregnancy filter, a liver disease or allergic reaction to the statin pharmaceutical composition filter, and an optional cyclosporine filter.

The computer system runs survey results against a second series of filters that each generates a warning where the subject's survey results identify a risk factor for the OTC statin. In some embodiments, the first series of filters includes one or more of: a total cholesterol level filter, a pooled cohort equation filter that incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value, the pooled cohort equation filter is deemed fired, an age filter, a drug interaction filter, an alcohol consumption filter, an adverse reaction filter, an atherosclerotic cardiovascular event filter, and an optional cyclosporine filter (e.g., when not included in the first series of filters).

The computer system then prompts the subject to acknowledge or deny having discussed these warnings with a medical professional (e.g., their physician). The computer system then proceeds with a fulfillment process only when (i) none of the first series of filters was fired (ii) the subject acknowledged that they discussed each warning issued in association with the second series of filters that was fired.

The computer system stores an indication of an initial order of the OTC statin in a subject profile, and communicates an over the counter drug facts label for the statin pharmaceutical composition to the subject. Upon confirmation from the subject that they have received and read the over the counter drug facts label, the computer system authorizes provision of the OTC statin pharmaceutical composition to the subject.

Example 3

A computer system is prepared for qualifying a human subject for delivery of a simvastatin pharmaceutical composition (e.g., low-dose Zocor) over the counter to treat or prevent an atherosclerotic cardiovascular disease (e.g., by lowering cholesterol). The computer system includes instructions for conducting a survey of the subject, to obtain one or more of: a sex of the subject, whether the subject is female and one of (i) pregnant, (ii) breastfeeding, or (iii) planning to become pregnant, whether the subject has or has ever had a liver disease, an age of the subject, a total cholesterol level of the subject, a HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications include cyclosporine, gemfibrozil, danazol, and/or a strong CYP3A4 inhibitor, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

The computer system runs survey results against a first series of filters that each prevents authorization for delivery of the OTC statin where the subject's survey results identify a contraindication for the OTC statin. In some embodiments, the first series of filters includes one or more of: a pregnancy filter, a liver disease or allergic reaction to the statin pharmaceutical composition filter, and an optional cyclosporine, gemfibrozil, danazol, and/or a strong CYP3A4 inhibitor filter.

The computer system runs survey results against a second series of filters that each generates a warning where the subject's survey results identify a risk factor for the OTC statin. In some embodiments, the first series of filters includes one or more of: a total cholesterol level filter, a pooled cohort equation filter that incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value, the pooled cohort equation filter is deemed fired, an age filter, a drug interaction filter, an alcohol consumption filter, an adverse reaction filter, an atherosclerotic cardiovascular event filter, and an optional cyclosporine, gemfibrozil, danazol, and/or a strong CYP3A4 inhibitor filter (e.g., when not included in the first series of filters).

The computer system then prompts the subject to acknowledge or deny having discussed these warnings with a medical professional (e.g., their physician). The computer system then proceeds with a fulfillment process only when (i) none of the first series of filters was fired (ii) the subject acknowledged that they discussed each warning issued in association with the second series of filters that was fired.

The computer system stores an indication of an initial order of the OTC statin in a subject profile, and communicates an over the counter drug facts label for the statin pharmaceutical composition to the subject. Upon confirmation from the subject that they have received and read the over the counter drug facts label, the computer system authorizes provision of the OTC statin pharmaceutical composition to the subject.

Example 4

A computer system is prepared for qualifying a human subject for delivery of a pravastatin pharmaceutical composition (e.g., low-dose PRAVACHOL) over the counter to treat or prevent an atherosclerotic cardiovascular disease (e.g., by lowering cholesterol). The computer system includes instructions for conducting a survey of the subject, to obtain one or more of: a sex of the subject, whether the subject is female and one of (i) pregnant, (ii) breastfeeding, or (iii) planning to become pregnant, whether the subject has or has ever had a liver disease, an age of the subject, a total cholesterol level of the subject, a HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications include cyclosporine, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

The computer system runs survey results against a first series of filters that each prevents authorization for delivery of the OTC statin where the subject's survey results identify a contraindication for the OTC statin. In some embodiments, the first series of filters includes one or more of: a pregnancy filter, a liver disease or allergic reaction to the statin pharmaceutical composition filter, and an optional cyclosporine filter.

The computer system runs survey results against a second series of filters that each generates a warning where the subject's survey results identify a risk factor for the OTC statin. In some embodiments, the first series of filters includes one or more of: a total cholesterol level filter, a pooled cohort equation filter that incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value, the pooled cohort equation filter is deemed fired, an age filter, a drug interaction filter, an alcohol consumption filter, an adverse reaction filter, an atherosclerotic cardiovascular event filter, and an optional cyclosporine filter (e.g., when not included in the first series of filters).

The computer system then prompts the subject to acknowledge or deny having discussed these warnings with a medical professional (e.g., their physician). The computer system then proceeds with a fulfillment process only when (i) none of the first series of filters was fired (ii) the subject acknowledged that they discussed each warning issued in association with the second series of filters that was fired.

The computer system stores an indication of an initial order of the OTC statin in a subject profile, and communicates an over the counter drug facts label for the statin pharmaceutical composition to the subject. Upon confirmation from the subject that they have received and read the over the counter drug facts label, the computer system authorizes provision of the OTC statin pharmaceutical composition to the subject.

Example 5

A computer system is prepared for qualifying a human subject for delivery of a fluvastatin pharmaceutical composition (e.g., low-dose LESCOL XL) over the counter to treat or prevent an atherosclerotic cardiovascular disease (e.g., by lowering cholesterol). The computer system includes instructions for conducting a survey of the subject, to obtain one or more of: a sex of the subject, whether the subject is female and one of (i) pregnant, (ii) breastfeeding, or (iii) planning to become pregnant, whether the subject has or has ever had a liver disease, an age of the subject, a total cholesterol level of the subject, a HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications include cyclosporine, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

The computer system runs survey results against a first series of filters that each prevents authorization for delivery of the OTC statin where the subject's survey results identify a contraindication for the OTC statin. In some embodiments, the first series of filters includes one or more of: a pregnancy filter, a liver disease or allergic reaction to the statin pharmaceutical composition filter, and an optional cyclosporine filter.

The computer system runs survey results against a second series of filters that each generates a warning where the subject's survey results identify a risk factor for the OTC statin. In some embodiments, the first series of filters includes one or more of: a total cholesterol level filter, a pooled cohort equation filter that incorporates the sex of the Example 6

A computer system is prepared for qualifying a human subject for delivery of a pitavastatin pharmaceutical composition (e.g., low-dose LIVALO) over the counter to treat or prevent an atherosclerotic cardiovascular disease (e.g., by lowering cholesterol). The computer system includes instructions for conducting a survey of the subject, to obtain one or more of: a sex of the subject, whether the subject is female and one of (i) pregnant, (ii) breastfeeding, or (iii) planning to become pregnant, whether the subject has or has ever had a liver disease, an age of the subject, a total cholesterol level of the subject, a HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications include cyclosporine, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

The computer system runs survey results against a first series of filters that each prevents authorization for delivery of the OTC statin where the subject's survey results identify a contraindication for the OTC statin. In some embodiments, the first series of filters includes one or more of: a pregnancy filter, a liver disease or allergic reaction to the statin pharmaceutical composition filter, and an optional cyclosporine filter.

The computer system runs survey results against a second series of filters that each generates a warning where the subject's survey results identify a risk factor for the OTC statin. In some embodiments, the first series of filters includes one or more of: a total cholesterol level filter, a pooled cohort equation filter that incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value the pooled cohort equation filter is deemed fired, an age filter, a drug interaction filter, an alcohol consumption filter, an adverse reaction filter, an atherosclerotic cardiovascular event filter, and an optional cyclosporine filter (e.g., when not included in the first series of filters).

The computer system then prompts the subject to acknowledge or deny having discussed these warnings with a medical professional (e.g., their physician). The computer system then proceeds with a fulfillment process only when (i) none of the first series of filters was fired (ii) the subject acknowledged that they discussed each warning issued in association with the second series of filters that was fired.

The computer system stores an indication of an initial order of the OTC statin in a subject profile, and communicates an over the counter drug facts label for the statin pharmaceutical composition to the subject. Upon confirmation from the subject that they have received and read the over the counter drug facts label, the computer system authorizes provision of the OTC statin pharmaceutical composition to the subject.

Example 7

A computer system is prepared for qualifying a human subject for delivery of a lovastatin pharmaceutical composition (e.g., low-dose MEVACOR) over the counter to treat or prevent an atherosclerotic cardiovascular disease (e.g., by lowering cholesterol). The computer system includes instructions for conducting a survey of the subject, to obtain one or more of: a sex of the subject, whether the subject is female and one of (i) pregnant, (ii) breastfeeding, or (iii) planning to become pregnant, whether the subject has or has ever had a liver disease, an age of the subject, a total cholesterol level of the subject, a HDL cholesterol count of the subject, a systolic blood pressure of the subject, a race of the subject, whether the subject is taking a high blood pressure medication, whether the subject is taking one or more medications that interact with the statin pharmaceutical composition, where the one or more medications include cyclosporine and a strong CYP3A4 inhibitor, a smoking status of the subject, a diabetes status of the subject, an alcohol consumption status of the subject, whether the subject has had an adverse reaction to a cholesterol lowering medication, and whether the subject has ever had an atherosclerotic cardiovascular event or had a heart procedure.

The computer system runs survey results against a first series of filters that each prevents authorization for delivery of the OTC statin where the subject's survey results identify a contraindication for the OTC statin. In some embodiments, the first series of filters includes one or more of: a pregnancy filter, a liver disease or allergic reaction to the statin pharmaceutical composition filter, and an optional cyclosporine and/or strong CYP3A4 inhibitor filter.

The computer system runs survey results against a second series of filters that each generates a warning where the subject's survey results identify a risk factor for the OTC statin. In some embodiments, the first series of filters includes one or more of: a total cholesterol level filter, a pooled cohort equation filter that incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease, where, when the risk satisfies a first threshold range or a first threshold value the pooled cohort equation filter is deemed fired, an age filter, a drug interaction filter, an alcohol consumption filter, an adverse reaction filter, an atherosclerotic cardiovascular event filter, and an optional cyclosporine and/or strong CYP3A4 inhibitor filter (e.g., when not included in the first series of filters).

The computer system then prompts the subject to acknowledge or deny having discussed these warnings with a medical professional (e.g., their physician). The computer system then proceeds with a fulfillment process only when (i) none of the first series of filters was fired (ii) the subject acknowledged that they discussed each warning issued in association with the second series of filters that was fired.

The computer system stores an indication of an initial order of the OTC statin in a subject profile, and communicates an over the counter drug facts label for the statin pharmaceutical composition to the subject. Upon confirmation from the subject that they have received and read the over the counter drug facts label, the computer system authorizes provision of the OTC statin pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of managing cholesterol in a human subject who was not previously qualified for delivery of an over the counter statin pharmaceutical composition, the method comprising:

a) receiving a request from the subject for the statin pharmaceutical composition, at a computer system having a processor programed to receive the request;
b) providing a survey for obtaining a plurality of survey results from the subject, via a computer system having a processor programed to perform the survey, wherein the plurality of survey results comprises:
   an age of the subject,
   a gender of the subject,
   when the subject is female, whether the subject is (i) pregnant, (ii) breastfeeding, or (iii) planning to become pregnant,
   a race of the subject,
   whether the subject is taking one or more medications that interact with the statin pharmaceutical composition, wherein the one or more medications include cyclosporine,
   whether the subject has ever had an atherosclerotic cardiovascular event or had a heart procedure;
   a total cholesterol level of the subject,
   an HDL cholesterol count of the subject,
   a systolic blood pressure of the subject,
   whether the subject is taking a high blood pressure medication,
   a diabetes status of the subject,
   a smoking status of the subject,
   whether the subject has liver disease,
   an alcohol consumption status of the subject,
   whether the subject has had an adverse reaction to a cholesterol lowering medication, and
c) receiving the plurality of survey results, at a computer system having a processor programed to receive the survey results;
d) applying an algorithm to the plurality of survey results, via a computer system having a processor programmed to perform the algorithm, wherein the algorithm:
   i) runs all or a portion of the plurality of survey results against a plurality of filters, wherein, when a respective filter in the plurality of filters is fired, the process is terminated or the subject is provided with a warning corresponding to the respective filter, and wherein the plurality of filters comprises:
      an age filter,
      a pregnancy filter,
      a drug interaction filter,
      an atherosclerotic cardiovascular event filter;
      a total cholesterol level filter,
      a pooled cohort equation filter,
      a liver disease filter,
      an alcohol consumption filter, and
      an adverse reaction filter,
   ii) obtains, when the process is not terminated, acknowledgment from the subject for each warning issued to the subject by any filter in the plurality of filters, and
   iii) proceeds with the process when (1) the process is not already terminated by the firing of a filter in the plurality of filters and (2) the subject has acknowledged each warning associated with each filter in the plurality of filters that was fired and that is associated with a warning, wherein the process further comprises:
      storing an indication in a subject profile of a re-order for the statin pharmaceutical composition,
      communicating an over the counter drug facts label for the statin pharmaceutical composition to the subject, and
      authorizing, upon confirmation from the subject that the over the counter drug facts label has been received and read, a provision of the statin pharmaceutical composition to the subject; and
e) administering the statin pharmaceutical composition to the human subject, upon authorization of the provision, to manage cholesterol in the human subject.

2. The method of claim 1, wherein the subject has a coronary heart disease, a cerebrovascular disease, a peripheral artery disease, or an aortic atherosclerotic disease.

3. The method of claim 1, wherein the age filter is fired when the plurality of survey results indicate that the subject is over the age of 75.

4. The method of claim 1, wherein when the age filter is fired the subject is provided with a warning.

5. The method of claim 1, wherein the pregnancy filter is fired when the plurality of survey results indicate that the subject is (i) pregnant, (ii) breastfeeding, or (iii) planning to become pregnant.

6. The method of claim 1, wherein when the pregnancy filter is fired the procedure is terminated.

7. The method of claim 1, wherein the drug interaction filter is fired when the plurality of survey results indicate the subject is taking an HIV/AIDS medication, colchicine, or a hepatitis medication.

8. The method of claim 1, wherein when the drug interaction filter is fired the subject is provided with a warning.

9. The method of claim 1, wherein the atherosclerotic cardiovascular event filter is fired when the plurality of survey results indicates the subject has had a heart attack, a stroke, or a heart procedure.

10. The method of claim 1, wherein when the atherosclerotic cardiovascular event filter is fired the subject is provided with a warning.

11. The method of claim 1, wherein the total cholesterol filter is fired when the plurality of survey results indicates the subject has a total cholesterol of less than 130 mg/dl.

12. The method of claim 1, wherein when the total cholesterol filter is fired the subject is provided with a warning.

13. The method of claim 1, wherein the pooled cohort equation filter is fired when the plurality of survey results indicates the subject has a 10-year risk of atherosclerotic cardiovascular disease of less than five percent.

14. The method of claim 1, wherein the pooled cohort equation filter incorporates the sex of the subject, the race of the subject, the age of the subject, the total cholesterol level of the subject, the HDL cholesterol count of the subject, the systolic blood pressure of the subject, whether the subject is taking a medication that interacts with a statin, the smoking status of the subject, and the diabetes status of the subject to derive a risk for the atherosclerotic cardiovascular disease.

15. The method of claim 1, wherein the pooled cohort equation is implemented as a multivariable Cox proportional hazard regression.

16. The method of claim 1, wherein when the pooled cohort equation filter is fired the subject is provided with a warning.

17. The method of claim 1, wherein:
   the liver disease filter is fired when the plurality of survey results indicate that subject has liver disease, and
   when the liver disease filter is fired, the process is terminated.

18. The method of claim 1, wherein the alcohol consumption filter is fired when the plurality of survey results indicates the subject consumes an average of three or more servings of alcohol per day.

19. The method of claim 1, wherein when the alcohol consumption filter is fired the subject is provided with a warning.

20. The method of claim 1, wherein the adverse reaction filter is fired when the plurality of survey results indicates the subject has had an adverse reaction to any cholesterol lowering medication.

21. The method of claim 1, wherein when the adverse reaction filter is fired the subject is provided with a warning.

22. The method of claim 1, wherein:
the plurality of survey results further comprises whether the subject has kidney disease, and
the plurality of filters includes a kidney disease filter that is fired when the plurality of survey results indicates the subject has kidney disease.

23. The method of claim 1, wherein
the plurality of filters includes an Asian descent filter that is fired when the plurality of survey results indicates the subject is of Asian descent.

24. The method of claim 1, wherein the statin pharmaceutical composition comprises lovastatin, fluvastatin, atorvastatin, rosuvastatin, simvastatin, pravastatin, or pitavastatin.

25. The method of claim 1, wherein the statin pharmaceutical composition comprises rosuvastatin and the subject is administered a daily dosage of from 4 mg to 11 mg.

26. The method of claim 1, wherein the statin pharmaceutical composition comprises atorvastatin and the subject is administered a daily dosage of 10 mg.

27. The method of claim 1, wherein the statin pharmaceutical composition comprises lovastatin and the subject is administered a daily dosage of from 15 mg to 25 mg.

28. The method of claim 1, wherein the statin pharmaceutical composition comprises simvastatin and the subject is administered a daily dosage of from 10 mg to 25 mg.

29. The method of claim 1, wherein, the statin pharmaceutical composition comprises pravastatin and the subject is administered a daily dosage of from 10 mg to 80 mg.

30. The method of claim 1, wherein the statin pharmaceutical composition comprises fluvastatin and the subject is administered a daily dosage of from 20 mg to 40 mg.

31. The method of claim 1, wherein the statin pharmaceutical composition comprises pitavastatin and the subject is administered a daily dosage of from 1 mg to 4 mg.

32. The method of claim 1, wherein the acknowledgment received from the subject, for each respective warning issued to the subject by any filter in the plurality of filters, is confirmation that the subject has discussed the respective warning with a physician.

33. The method of claim 1, wherein:
at least two of the filters in the plurality of filters, when fired terminate the process; and
at least two of the filters in the plurality of filters, when fired provide the subject with a warning.

* * * * *